United States Patent

Mooberry et al.

Patent Number: 6,132,944
Date of Patent: Oct. 17, 2000

[54] PHOTOGRAPHIC ELEMENT CONTAINING HIGH DYE-YIELD COUPLERS

[75] Inventors: Jared B. Mooberry, Rochester; Steven M. Bonser, Fairport; Kevin P. Dockery; David Hoke, both of Rochester; Chang-Kyu Kim, Pittsford; James J. Seifert, Hilton; David T. Southby, Rochester, all of N.Y.; Zheng Z. Wu, Woodbury, Minn.

[73] Assignee: Eastman Kodak Company, Rochester, N.Y.

[21] Appl. No.: 09/433,256

[22] Filed: Nov. 4, 1999

Related U.S. Application Data

[63] Continuation of application No. 09/224,899, Dec. 31, 1998, abandoned.

[51] Int. Cl.[7] ............................... G03C 1/08; G03C 7/26; G03C 7/32
[52] U.S. Cl. ..................... 430/543; 430/555; 430/955; 430/958; 430/226; 430/359
[58] Field of Search ................................. 430/226, 359, 430/543, 557, 955, 958

[56] References Cited

U.S. PATENT DOCUMENTS

| | | | |
|---|---|---|---|
| 4,248,962 | 2/1981 | Lau | 430/382 |
| 4,840,884 | 6/1989 | Mooberry et al. | 430/557 |
| 5,447,819 | 9/1995 | Mooberry et al. | 430/226 |
| 5,457,004 | 10/1995 | Mooberry et al. | 430/226 |
| 5,612,173 | 3/1997 | Proehl et al. | 430/504 |
| 5,830,632 | 11/1998 | Chari et al. | 430/546 |
| 5,998,121 | 12/1999 | Southby et al. | 430/543 |
| 6,007,973 | 2/1999 | Southby et al. | 430/496 |

*Primary Examiner*—Geraldine Letscher
*Attorney, Agent, or Firm*—Arthur E. Kluegel

[57] ABSTRACT

Disclosed is a photographic element containing a light sensitive silver halide emulsion layer having associated therewith a coupler represented by Formula I:

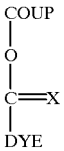

I wherein
COUP is a coupler parent group capable of reacting with an oxidized developer to form a first dye and is bonded at a coupling position to the group

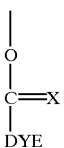

wherein X is a or $NSO_2R$; R is an alkyl or aryl group; and DYE is a releasable second dye that is after release the same color as the first dye and is linked to OC=X by a moiety of the DYE having Formula (IA):

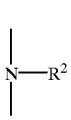

IA wherein $R^2$ is a substituent;
provided there is contained in the coupler of Formula I at least one group of Formula IB:

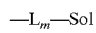

IB wherein L is a divalent linking group and m is 0 or 1; and Sol is a group containing an acidic hydrogen selected from the group consisting of —ArOH, —$NHSO_2R^1$ and —$SO_2NHR^1$, in which AR is an aromatic group and each $R^1$ is a substitute;
provided further that the pKa of an acidic hydrogen of Sol is less than 8.8.

30 Claims, No Drawings

PHOTOGRAPHIC ELEMENT CONTAINING HIGH DYE-YIELD COUPLERS

CROSS REFERENCE TO RELATED APPLICATIONS

This application is a continuation of copending U.S. Ser. No. 09/224,899, filed Dec. 31, 1998, now abandoned.

FIELD OF THE INVENTION

This invention relates to a photographic element containing a silver halide emulsion layer and an associated improved reactivity high dye-yield coupler that contains a release dye bonded through an acyloxy type group at the coupling site where the coupler contains an arylhydroxy, sulfamoyl or sulfonamido group of pKa less than 8.8.

BACKGROUND OF THE INVENTION

Useful high dye-yield (HDY) couplers have been disclosed by Moobenry and Singer in U.S. Pat. No. 4,840,884. Such couplers react with oxidized color developer to form one dye and in doing so release a precursor of a second dye. The patent provides examples (Example 38 and 40) of hydrophilic sulfonamide solubilization of the coupler. Example 39 incorporates a sulfonamide in the coupler as well as carboxyl solubilization in the dye moiety for enhanced reactivity. It has been found, however, that couplers of this type, particularly those containing a coupler portion capable of forming a yellow dye upon coupling with oxidized developer, are often unsatisfactory from the standpoint of reactivity.

Reactivity improvements can be obtained in couplers of this type which contain timing groups as disclosed in U.S. Pat. No. 5,447,819. These couplers have the general formula COUP—(T)$_m$—L—DYE and particular solubilizing groups are incorporated in the timing group (T) to enhance reactivity. It has been found however that such couplers containing a timing group present other problems. In particular, such couplers have been found to cause dark keeping problems. It is believed that the described high dye-yield coupler can be unstable during keeping and can be oxidized in ambient surroundings. This oxidation results in the release of the DYE portion of the coupler which then shifts from colorless to yellow colored and this is an unacceptable result.

U.S. Pat. No. 5,457,004 describes high dye yield couplers having methine dye chromophores. Several of the described couplers (I-4, I-5, I-46, I-57 and I-60) disclose acyloxy links between the COUP and DYE groups. All contain sulfonamide-solubilized coupler moieties. Example I-60 incorporates a carboxyl group in the dye moiety as well. The sulfonamide couplers have proved to be less reactive than desired toward color developer.

A problem to be solved is to provide a silver halide photographic element containing a stable high dye-yield coupler that will exhibit a higher reactivity with oxidized developer than couplers heretofore discovered.

SUMMARY OF THE INVENTION

The invention provides a photographic element containing a light sensitive silver halide emulsion layer having associated therewith a coupler represented by Formula I:

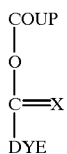

I wherein

COUP is a coupler parent group capable of reacting with an oxidized developer to form a first dye and is bonded at a coupling position to the group

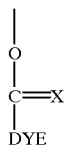

wherein X is O or NSO$_2$R; R is an alkyl or aryl group, and DYE is a releasable second dye that is after release the same color as the first dye and is linked to OC=X by a moiety of the DYE having Formula (IA):

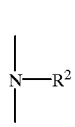

IA wherein R$^2$ is a substituent;
provided there is contained in the coupler of Formula I at least one group of Formula IB:

   IB wherein L is a divalent linking group and m is 0 or 1; and Sol is a group containing an acidic hydrogen selected from the group consisting of —ArOH, —NHSO$_2$R$^1$ and —SO$_2$NHR$^1$, in which Ar is an aromatic group and each R$^1$ is a substituent;
and provided further that the pKa of an acidic hydrogen of Sol is less than 8.8.

The invention also provides a coupler of the described formula, and an imaging method comprising exposing the element of the invention to light and thereafter contacting the element with a color developer.

The silver halide photographic element contains a stable high dye-yield coupler that will exhibit a higher reactivity with oxidized developer than couplers heretofore discovered.

DETAILED DESCRIPTION OF THE INVENTION

As described in the Summary of the Invention, the invention provides a photographic element containing a light sensitive silver halide emulsion layer having associated therewith a coupler represented by Formula I.

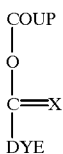

COUP of the invention is the parent portion of the coupler. This is the portion of the coupler that combines with oxidized color developer in a conventional process to form a colored image dye. The various types of couplers are described more fully hereinafter. Typical COUP groups form yellow dyes (e.g. acylacetanilides), magenta dyes (e.g. pyrazolones or pyrazoloazoles, or cyan dyes (e.g. phenols, naphthols or pyrazoloazoles). In the preferred embodiment of the invention the COUP group is one which forms a yellow dye such as an acylacetanilide. Suitable examples include pivaloylacetanilides, methylcyclopropylacetanilides, indoloylacetanilides, and benzoylacetanilides.

X may be an oxygen atom or the group $NSO_2R$, where R is an alkyl or aryl group. Typically X is O which renders the linking group between COUP and DYE an acyloxy group. Equivalently, the linking group may be viewed as a carbamyloxy group when the necessary N linkage of DYE is considered. If X is a sulfonimido group, then the linking group between COUP and DYE would be considered a sulfonylisocyanato group. For simplicity, discussion herein may be directed to the acyloxy or carbarnyloxy group but is intended to apply equally to the situation where X is the sulfonylisocyanato group.

DYE is a dye of the same color as that formed by COUP upon reaction with oxidized developer. Suitably, DYE is yellow colored. When the yellow DYE is appended to the coupler through the acyloxy group, it is conveniently shifted to the invisible UV range and thus remains invisible unless and until detached from COUP in an imagewise fashion. DYE may be any of the DYE types specified in U.S. Pat. No. 4,840,884. Desirably these DYE groups are azo- or methine dyes. Useful embodiments include the methine dyes as described in U.S. Pat. No. 5,457,004.

One useful embodiment of DYE has the formula:

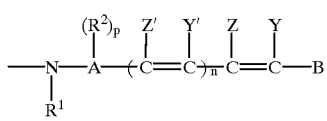

$R^1$ is hydrogen or a substituted or unsubstituted alkyl or aryl (including heteroaryl) group. The $R^1$ substituent can be any substituent that does not adversely affect the coupler. $R^1$ can be, for example, hydrogen or alkyl, such as alkyl containing 1 to 42, typically 1 to 22 carbon atoms. Preferred $R^1$ groups are unsubstituted or substituted allyl, such as alkyl containing 1 to 18 carbon atoms or unsubstituted or substituted aryl, such as phenyl. Suitably, $R^1$ may be methyl, ethyl, propyl, butyl, pentyl, docecyl etc. Cyclic or branched alkyl groups such as isopropyl, cyclopentyl or cyclohexyl have been found advantageous as have alkyl groups of 1 to 5 carbon atoms.

A is a substituted or unsubstituted aryl (including heteroaryl) ring containing up to three optional substituents $R^2$. Suitably, A is a phenyl, naphthyl, or thiazole ring. Each $R^2$ is independently a substituted or unsubstituted alkyl group which may form a ring with Z', and p is an integer from 0 to 3. One or more $R^2$ substituents may be present which preferably include alkyl groups of from 1 to 5 carbon atoms such as a methyl or propyl group.

Each Z, Z', and Y' is independently hydrogen or a substituent. Y is an electron withdrawing group. By electron withdrawing it is meant that the Hammett's sigma(para) constant value for Y is greater than zero. Constant values for various substituents are provided in Hansch and Leo, *Substituent Constants for Correlation Analysis in Chemistry and Biology*, Wiley, New York, 1979. Preferably, Y is a substituent having a Harnmett's sigma(para) constant value of at least 0.3 and most preferably at least 0.4. Suitable examples are cyano, carboxyl, sulfonyl, and acyl groups.

n, which represents the number of conjugated vinyl groups and affects the hue of the dye, is 0, 1, or 2.

B is a heterocycle having the formula:

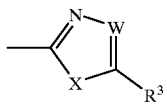

X is O, S, or $N(R^5)$ where $R^5$ is hydrogen or alkyl of up to 22 carbon atoms. Most suitably, X is O. W is N or $C(R^4)$ where $R^4$ is hydrogen or a substituent. $R^3$ is a substituent linked to the heterocycle by a carbon or nitrogen atom of the substituent. Suitably, $R^3$ is a substituted or unsubstituted alkyl or aryl group. If desired, $R^3$ and $R^4$ may be linked to form a ring. It is provided that $R^3$ and $R^4$ may be linked to form a ring and provided further that when $R^3$ and $R^4$ form a phenyl ring, Z is hydrogen, W is $C(R^4)$, and X is oxygen, the phenyl ring does not contain a substituent having a Hammett's sigma(para) value of 0.23 or more. The strong electron withdrawing power of such combination is believed responsible for the instability of couplers bearing such a combination of substituents.

When $R^3$ and $R^4$ form a ring, a substituted or unsubstituted ring, particularly an aromatic ring, may be employed. Phenyl and naphthyl rings are examples. The ring may suitably contain one or more substituents of up to 20 carbon atoms each such as alkyl groups, e.g. methyl, i-propyl, t-butyl etc.

In a preferred embodiment, X is O, W is $C(R^4)$, and $R^3$ and $R^4$ form a phenyl ring so that B is a benzoxazole group.

The DYE is bonded to the acyloxy liking group through the $-NR^2-$ group of the DYE. The $R^2$ group is preferably a substituent group rather than hydrogen. Desirably, it is an alkyl or aryl group, suitably one of C-18 or less. Suitable examples are methyl, ethyl, and branched alkyl of up to 8 carbon atoms. The selection of this substituent can have a significant effect on the resulting hue of DYE.

The first and second dyes are the same color in a high dye-yield coupler. By the same color it is meant they have an absorption maximum within 75 nm of each other. Typically, they are each yellow, magenta or cyan in color. Suitably they are yellow in color. The first dye is not formed until the development process. The second dye is shifted to the non-visible region so long as DYE is bonded to the rest of the coupler via OC=X but becomes colored upon release.

Sol may be bonded directly or indirectly to any portion of the coupler, either the COUP or DYE or X portion. It may be bonded through a divalent link, L, (which link could alternatively be considered a part of the COUP or DYE). The value of m being 0 or 1 signifies the optional nature of this L group. The Sol group is an —ArOH, —NHSO$_2$R$^1$, or —SO$_2$NH$^1$ group containing an acidic hydrogen which group has a pKa of less than 8.8. It is important that the group have such a low pKa in order to provide the desired reactivity to the coupler. If the COUP group will not release the acyloxy-DYE group, COUP cannot react to form image dye and the DYE group will not shift to the visible range. As witnessed by the comparative examples, not all —ArOH, —NHSO$_2$R$^1$, or —SO$_2$NHR$^1$ groups have the necessary pKa value. These groups must bear the indicated acidic hydrogen on the oxygen or nitrogen atom. It is generally desirable to provide electron-withdrawing substituents close to the proton bearing nitrogen in order to achieve the desired pKa. The precise strength and location of such substituents cannot be predicted exactly, but estimates can lead to the desired pKa values. It is desirable that the pKa be not less than 5 so that the coupler will not undesirably migrate during film manufacture and storage. Suitably, the range desired for pKa of the group is from 5.5 to 8.5 with a range of 6.0 to 8.0 being typically useful.

While carboxyl solubilization may enhance reactivity of the coupler (see comparative data section), it is not a desirable solubilizing group for other reasons. Because the carboxyl group is very acidic (pKa less than 5), it ionizes readily to the nucleophilic carboxylate ion which frequently interferes in acylation and alkylation reactions employed in the synthesis of high dye-yield couplers. Consequently, it usually requires protection/deprotection chemistry which adds cost and complexity to the synthesis. It also imparts crystalline character to couplers which can make them hard to disperse in a photographic element. Because it is a relatively strong acid, the carboxyl group can be responsible for acid-catalyzed hydrolysis reactions of the dyes in the film resulting in poor dye stability characteristics. Further, the dyes are subject to excessive wash out of the film even during neutral water rinse steps in the process.

The Ar group may be any carbocyclic or heterocyclic aromatic group. Ar is conveniently a phenyl group, rendering the Sol group a phenol compound. Phenol groups typically have aqueous pKa values generally in the range of 7 to 10 and are typically only partially ionized in pH 10 film development processes. The anion is quite nucleophilic, however, and can give the same problems in synthesis as carboxyl unless sterically hindered. In addition, phenols can couple with oxidized developer to give undesired blue dyes unless the phenolic coupling site is inaccessible.

Sulfonamido and sulfamoyl are hydrophilic groups which impart reactivity increases in the un-ionized form but become more effective when ionized. These groups commonly used in couplers are usually only partially ionized in the photographic process because of their relatively high pKa value (9–13) of the process and the effect of coupler partitioning into the oil phase. They have desirable characteristics, however. The ionized form is generally not very nucleophilic (sterically shielded) and does not usually interfere during synthesis. Because they are weaker acids than carboxylic acids, they do not promote hydrolysis reactions and do not significantly affect dye stability. The R$^1$ group of the sulfarnoyl or sulfonamide may be any alkyl or aryl group. Typically, Sol and L are such that there is bonded to the nitrogen atom bearing the acidic hydrogen an aromatic ring, such as one containing an electron withdrawing substituent.

Examples of useful COUP groups are:

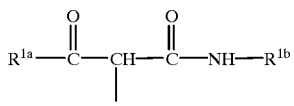

1A

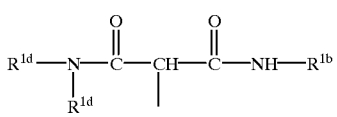

1B

A free bond from the coupling site in the above formulae indicates a position to which the coupling release group or coupling-off group is linked. In the above formulae, when R$^{1a}$ or R$^{1b}$ contains a ballast or anti-diffusing group, it is selected so that the total number of carbon atoms is from 8 to 32 and preferably from 10 to 22.

R$^{1a}$ represents an aliphatic- or alicyclic-hydrocarbon group, an aryl group, an alkoxyl group, or a heterocyclic group, and each R$^{1b}$ independently represents an aryl group or a heterocyclic group.

The aliphatic- or alicyclic hydrocarbon group represented by R$^{1a}$ preferably has at most 22 carbon atoms, may be substituted or unsubstituted, and aliphatic hydrocarbon may be straight or branched. These substituents may be further substituted with at least one of these substituents repeatedly. Useful examples of the groups as R$^{1a}$ include an isopropyl group, an isobutyl group, a tert-butyl group, an isoamyl group, a tert-amyl group, a 1,1-dimethyl-butyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an α-aminoisopropyl group, an α-(diethylamino)isopropyl group, an α-(succinimido) isopropyl group, an α-(phthalimido)isopropyl group, an α-(benzenesulfonamido)isopropyl group, and the like.

When R$^{1a}$ or R$^{1b}$ is an aryl group (especially a phenyl group), the aryl group may be substituted. The aryl group (e.g., a phenyl group) may be substituted with groups having not more than 32 carbon atoms such as an alkyl group, an alkenyl group, an alkoxy group, an alkoxycarbonyl group, an alkoxycarbonylamino group, an aliphatic- or alicyclic-amido group, an alkylsulfamoyl group, an alkylsulfonamido group, an alkylureido group, an aralkyl group and an alkyl-substituted succinimido group. This phenyl group in the aralkyl group may be further substituted with groups such as an aryloxy group, an aryloxycarbonyl group, an arylcarbamoyl group, an arylamido group, an arylsulfamoyl group, an arylsulfonamido group, and an arylureido group.

The phenyl group represented by R$^{1a}$ or R$^{1b}$ may be substituted with an amino group which may be further substituted with groups such as a nitro group, a cyano group, a thiocyano group, or a halogen atom.

R$^{1a}$ or R$^{1b}$ may represent substituents resulting from condensation of a phenyl group with other rings, such as a naphthyl group, a quinolyl group, an isoquinolyl group, a chromanyl group, a coumaranyl group, and a tetrahydronaphthyl group. These substituents may be further substituted repeatedly with at least one of above-described substituents for the phenyl group represented by R$^{1a}$ or R$^{1b}$.

When R$^{1a}$ represents an alkoxy group, the alkyl moiety of the alkoxyl group can be a straight or branched alkyl group, an alkenyl group, a cycloalkyl group, or a cycloalkenyl group each having at most 32 carbon atoms, preferably at most 22 carbon atoms. These substituents may be substituted with groups such as halogen atom, an aryl group and an alkoxyl group to form a group having at most 32 carbon atoms.

When $R^{1a}$ or $R^{1b}$ represents a heterocyclic ring, the heterocyclic group is linked to a carbon atom of the carbonyl group of the acyl group in α-acylacetamido or to a nitrogen atom of the amido group through one of the carbon atoms constituting the ring. Examples of such heterocyclic rings are thiophene, furan, pyran, pyrrole, pyrazole, pyridine, pyrazine, pyrimidine, pyridazine, indolizine, imidazole, thiazole, oxazole, triazine, thiadiazine and oxazine. These groups may further have a substituent or substituents in the ring thereof. Examples of the substituents include those defined for the aryl group represented by $R^{1a}$ and $R^{1b}$.

The following are examples of couplers useful in the photographic element of the invention.

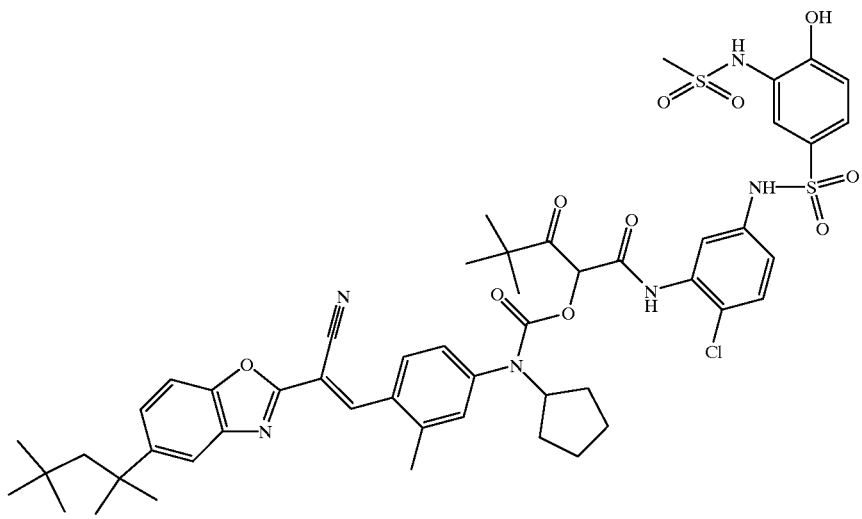

Inv-1

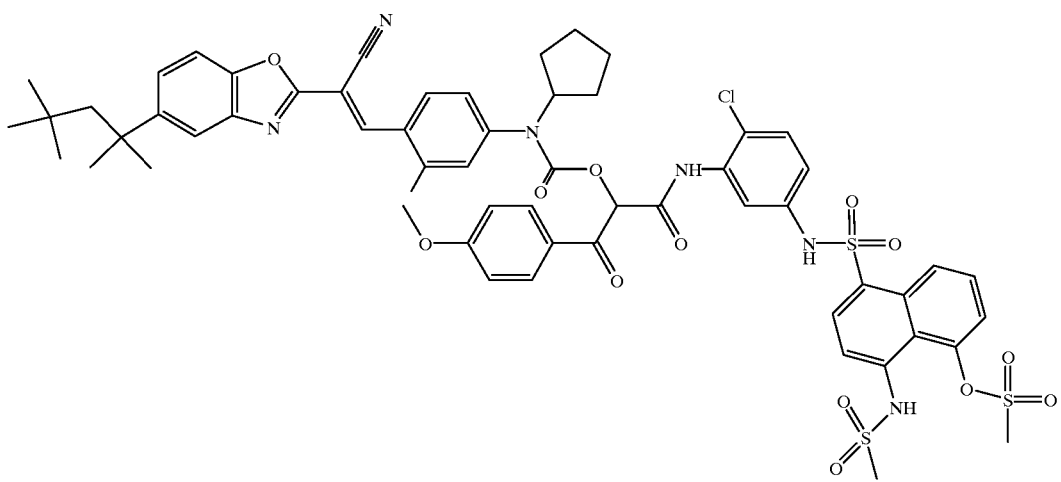

Inv-2

-continued
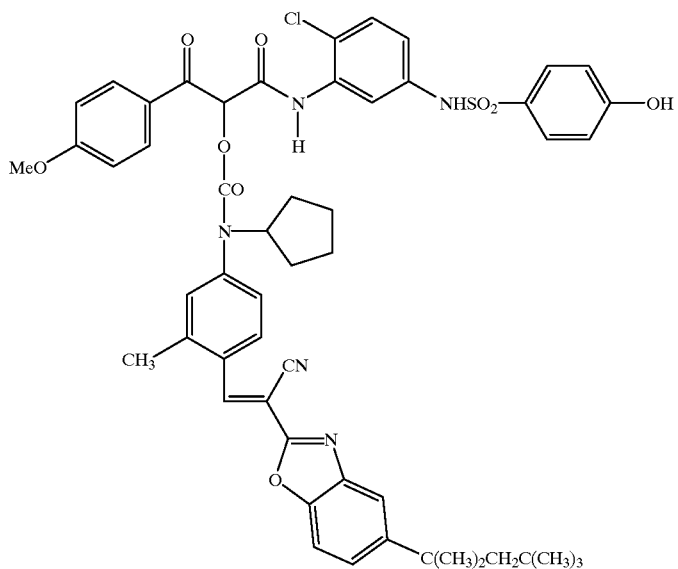
Inv-3
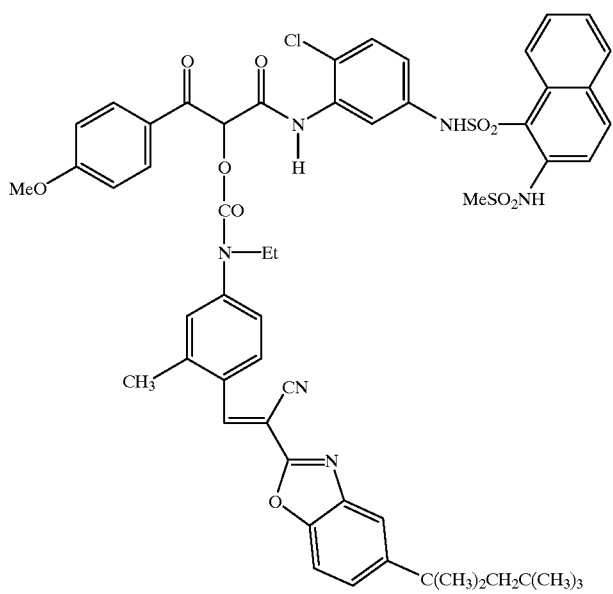
Inv-4

Inv-5
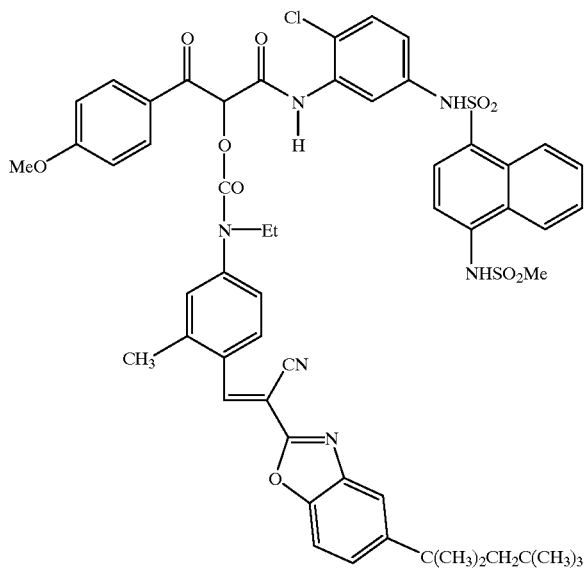
Inv-6
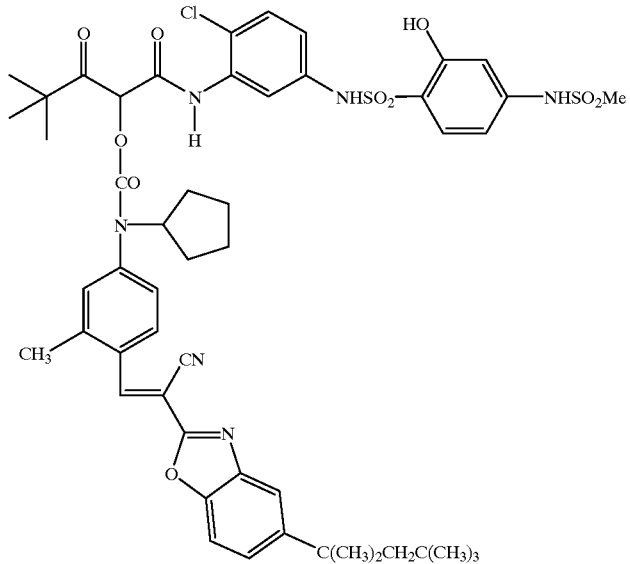

-continued
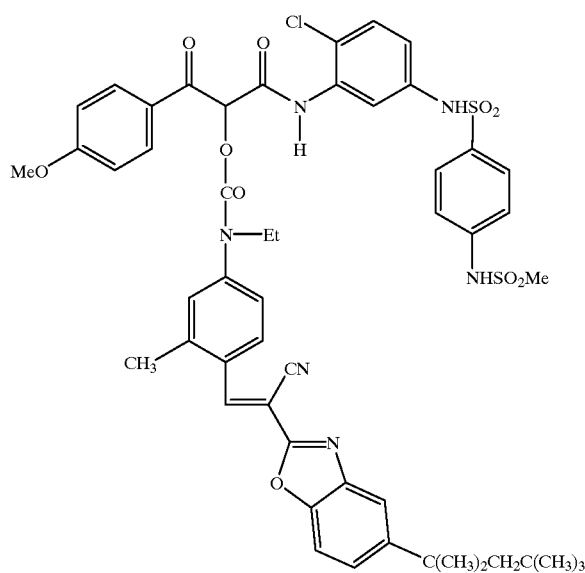
Inv-7
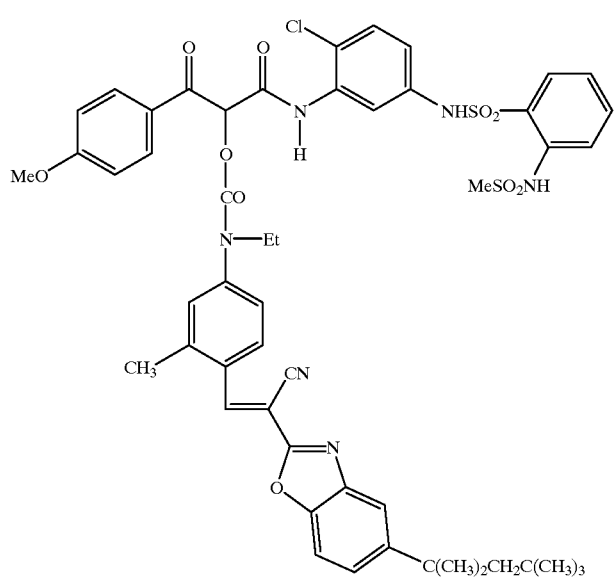
Inv-8

-continued
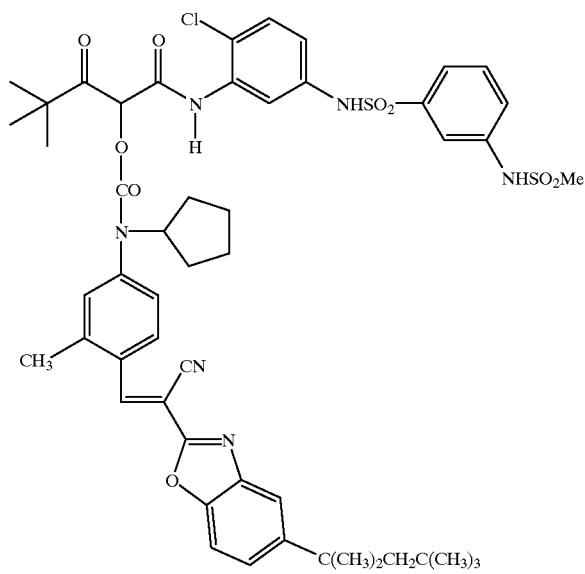
Inv-9
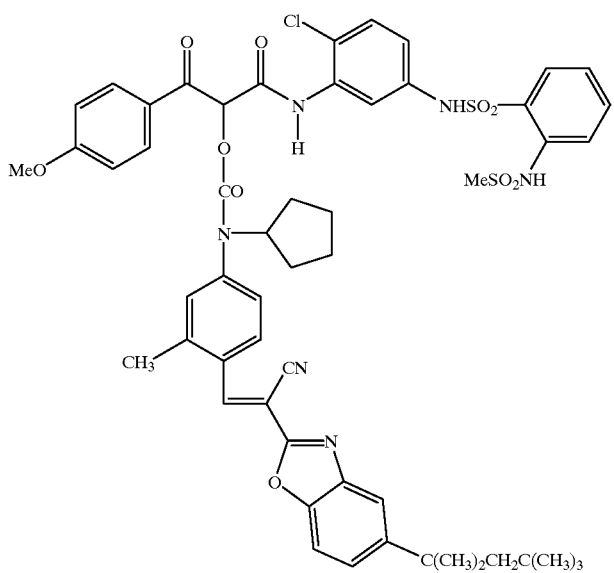
Inv-10

-continued
Inv-11
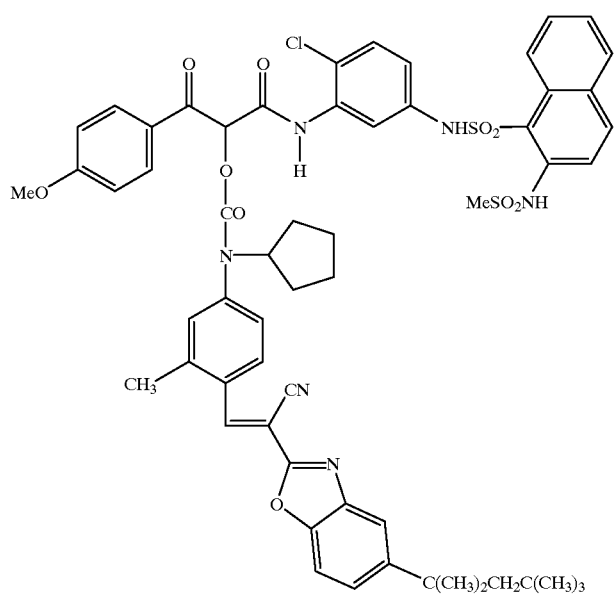
Inv-12
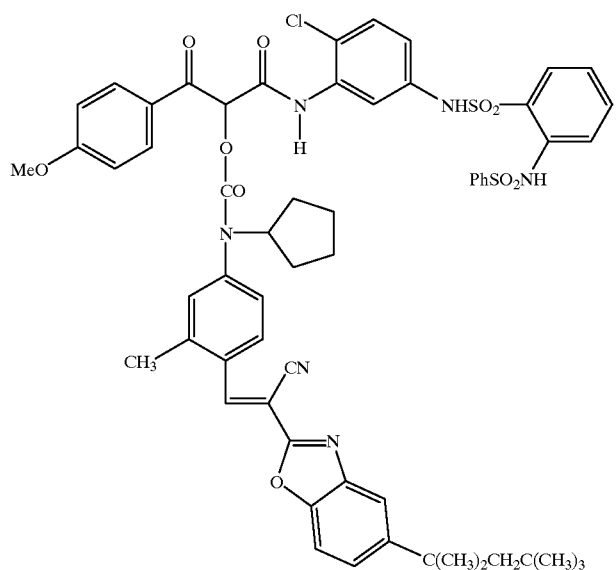

Inv-13
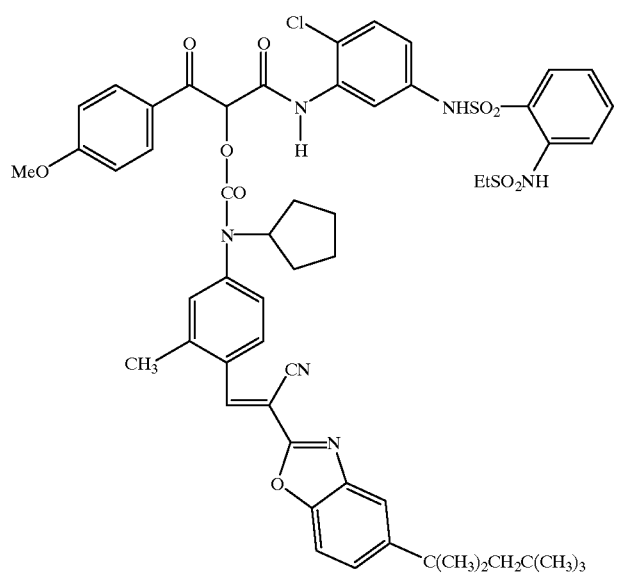
Inv-14
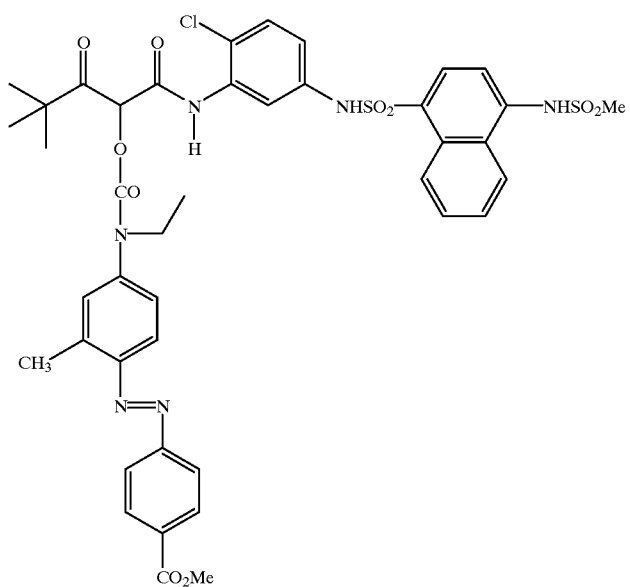

-continued
Inv-15
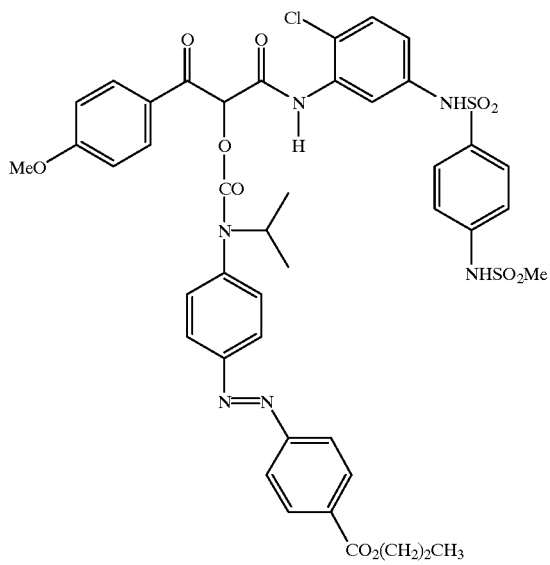
Inv-16
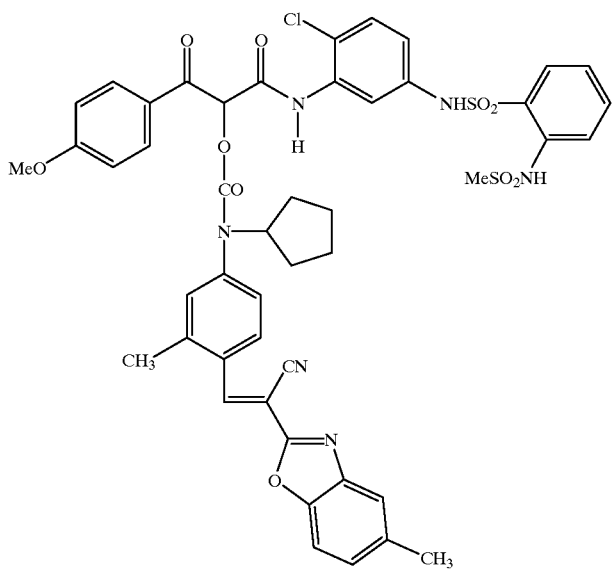

-continued
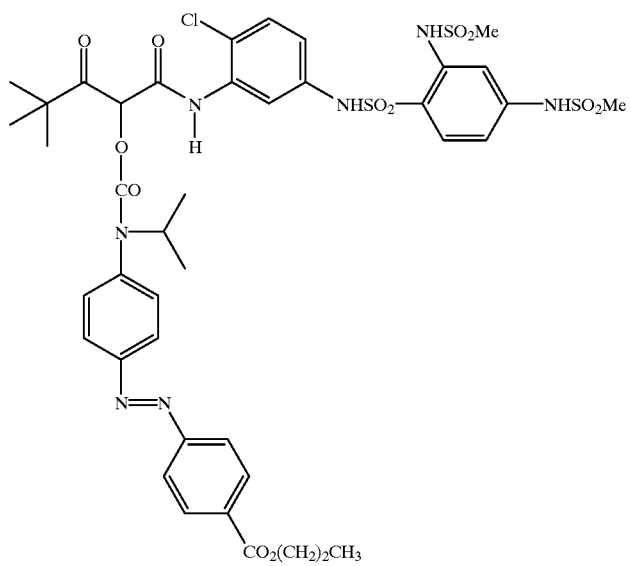
Inv-17
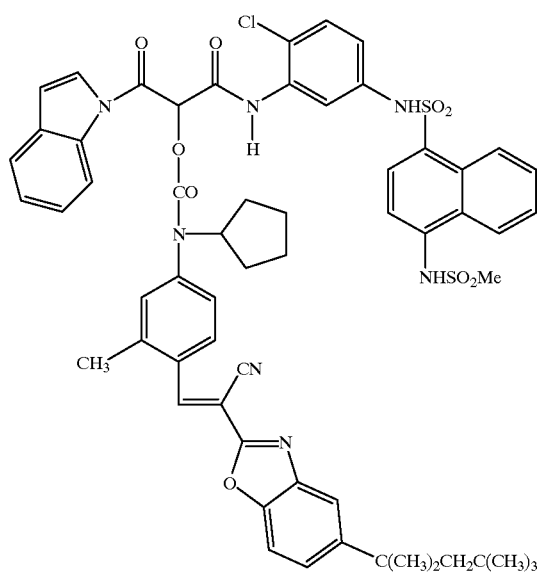
Inv-18

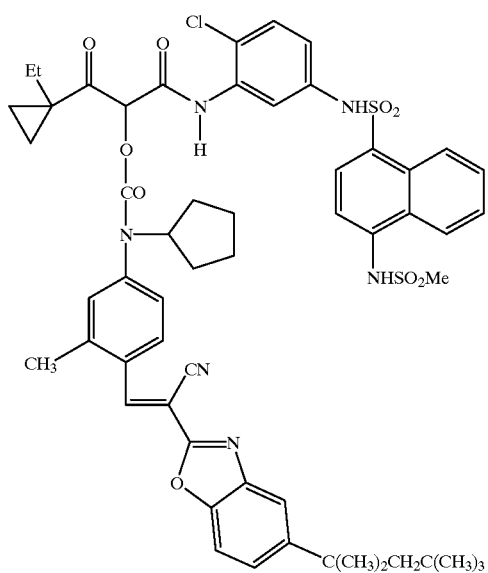
Inv-19
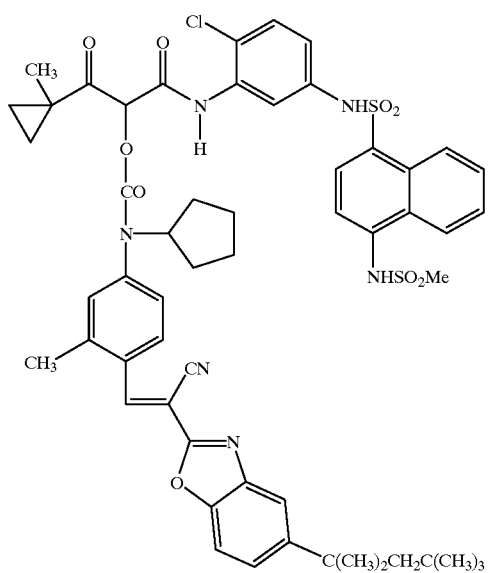
Inv-20

-continued
Inv-21
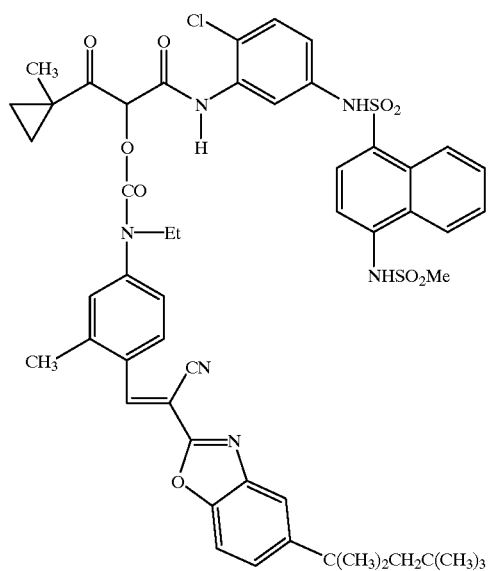
Inv-22
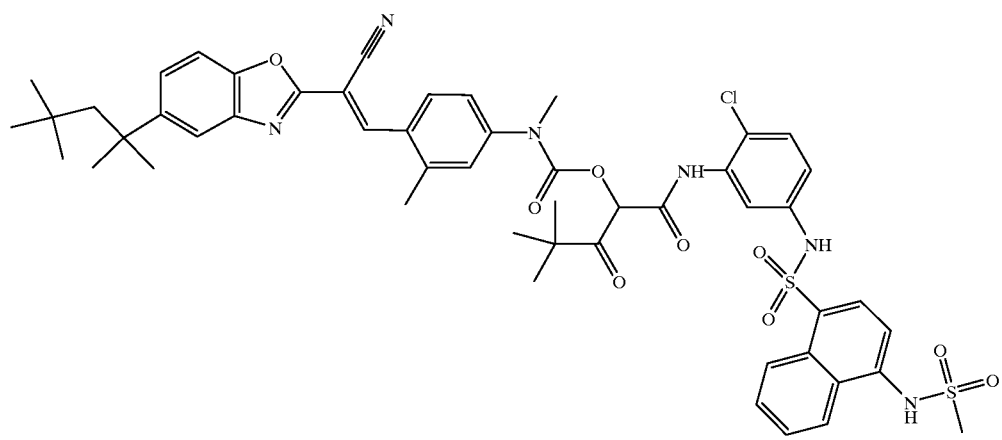
Inv-23
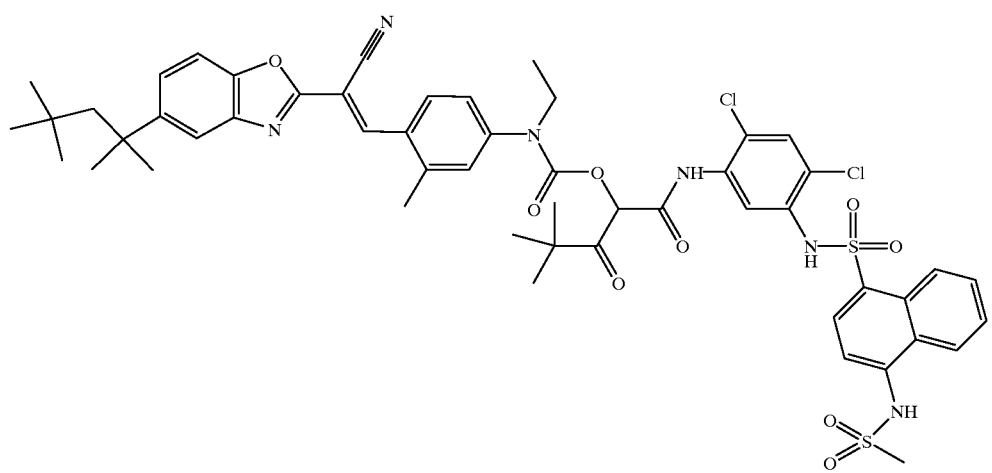

Inv-24
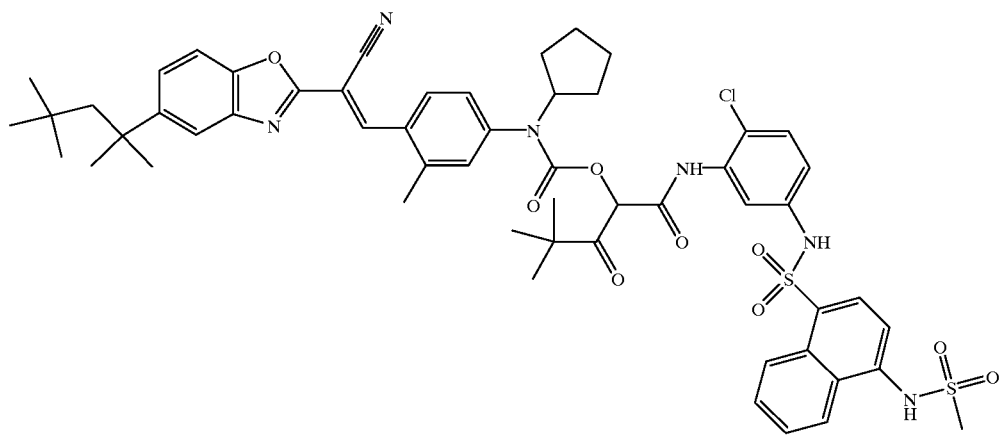
Inv-25
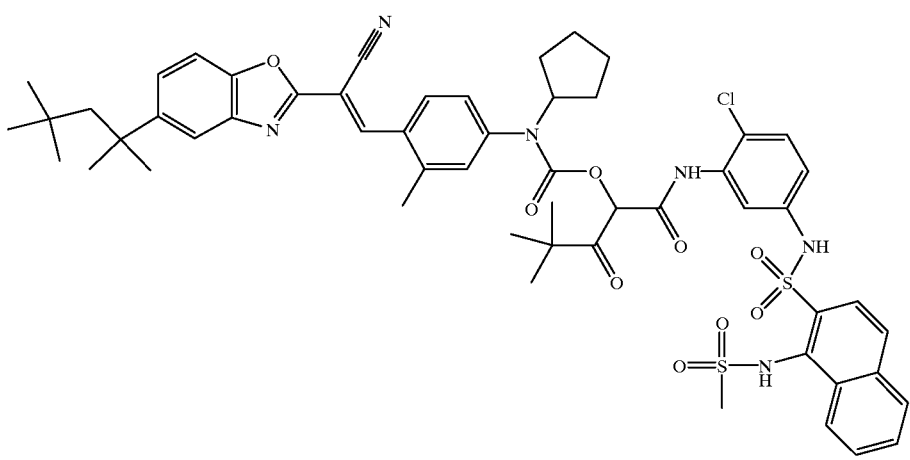
Inv-26
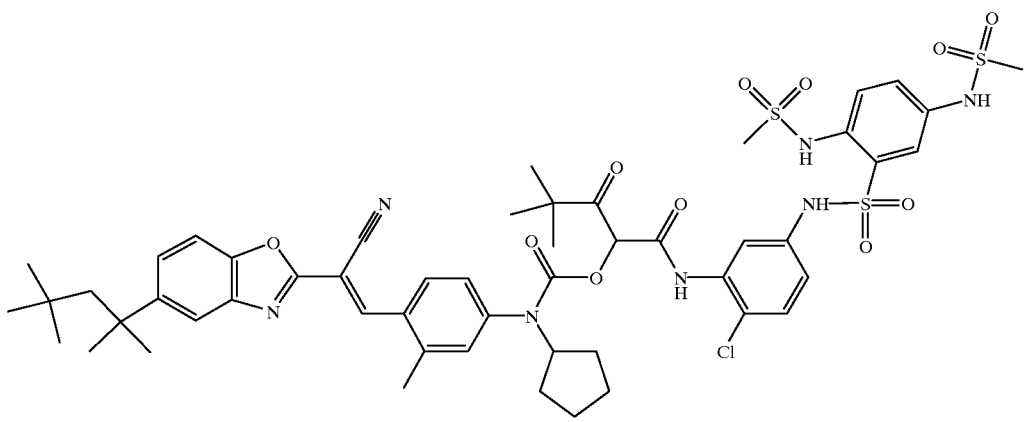

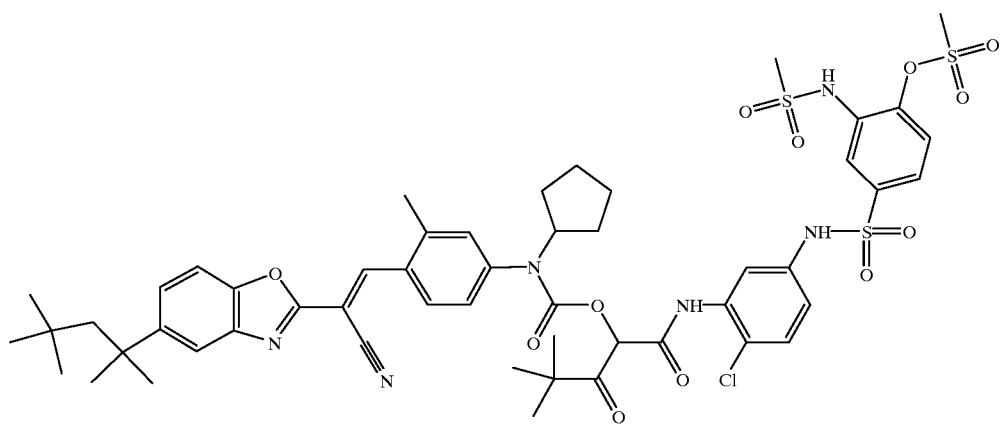
Inv-27
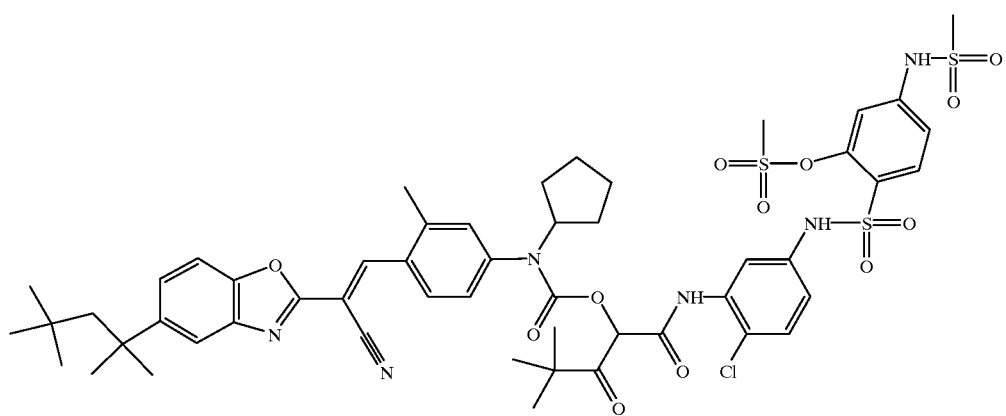
Inv-28
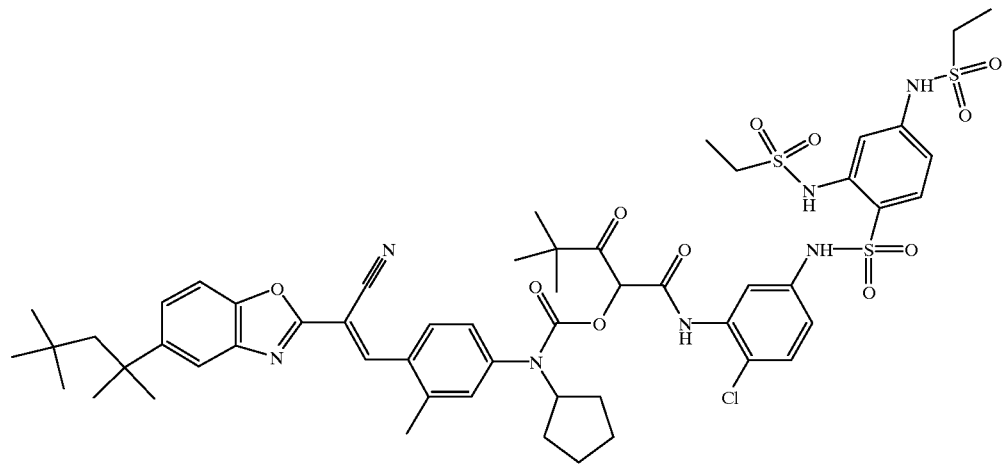
Inv-29

-continued
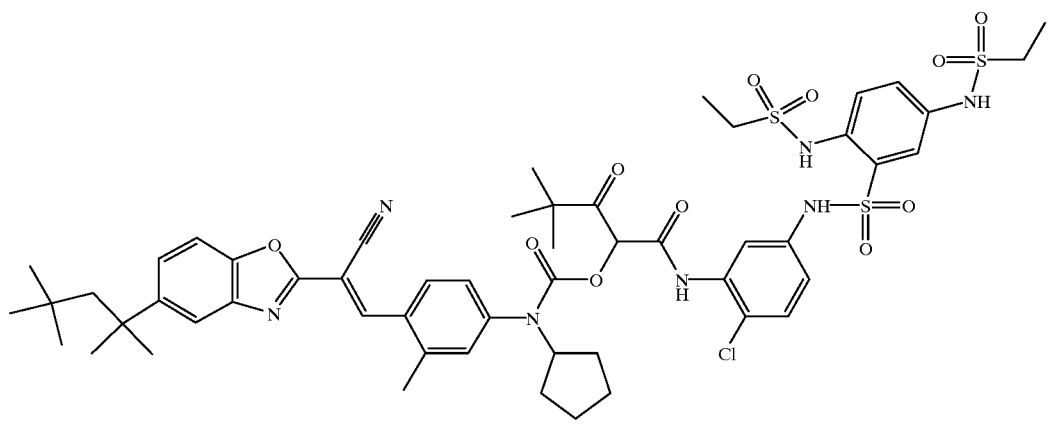
Inv-30
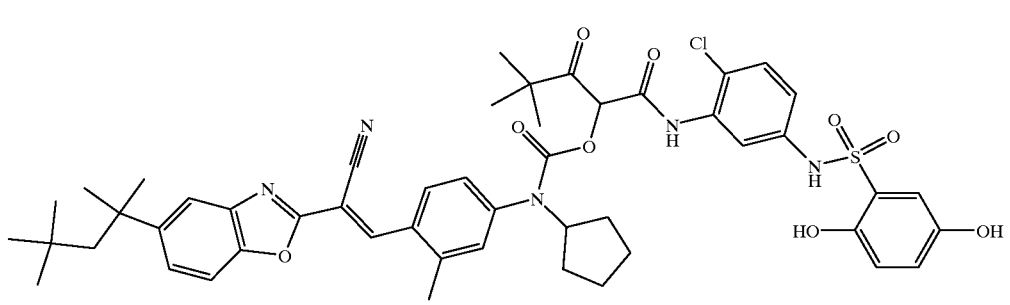
Inv-31
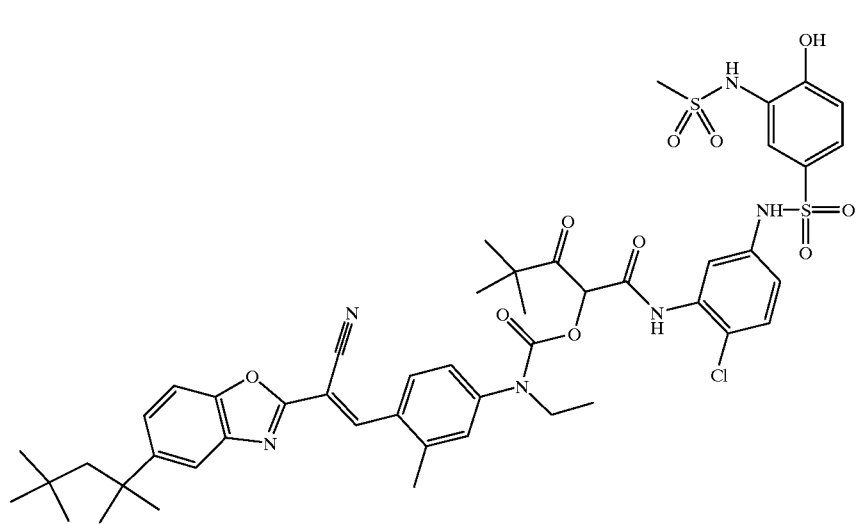
Inv-32
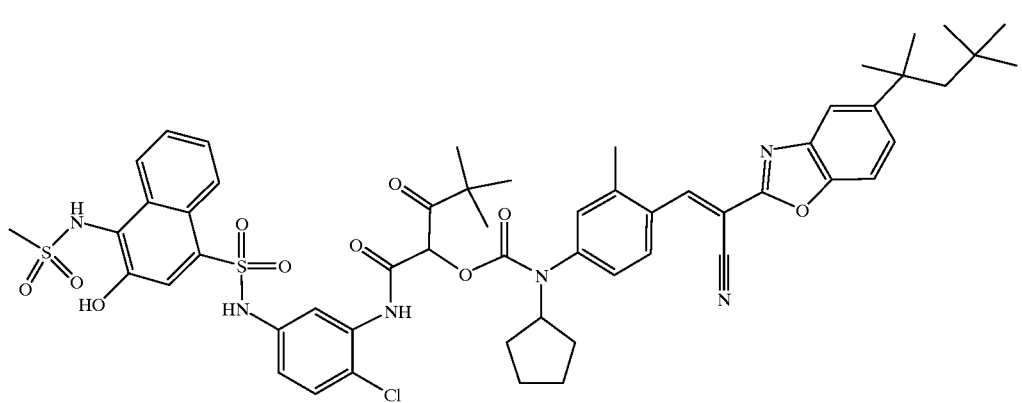
Inv-33

-continued
Inv-34
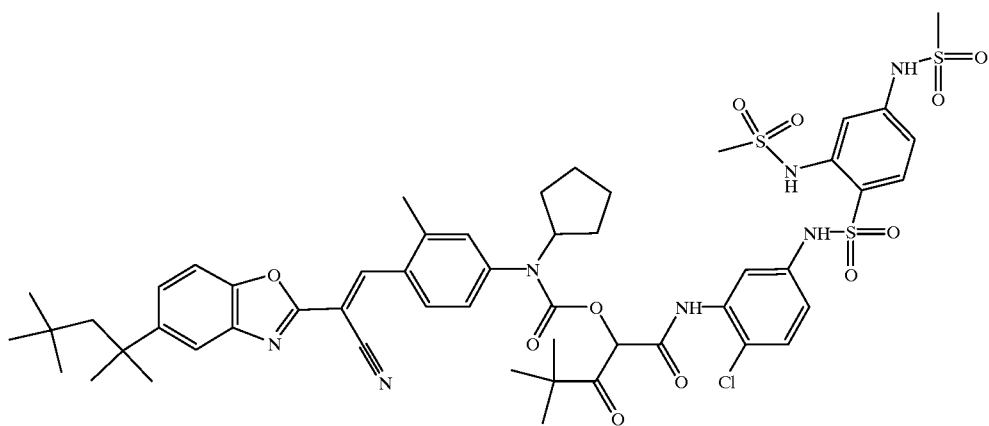
Inv-35
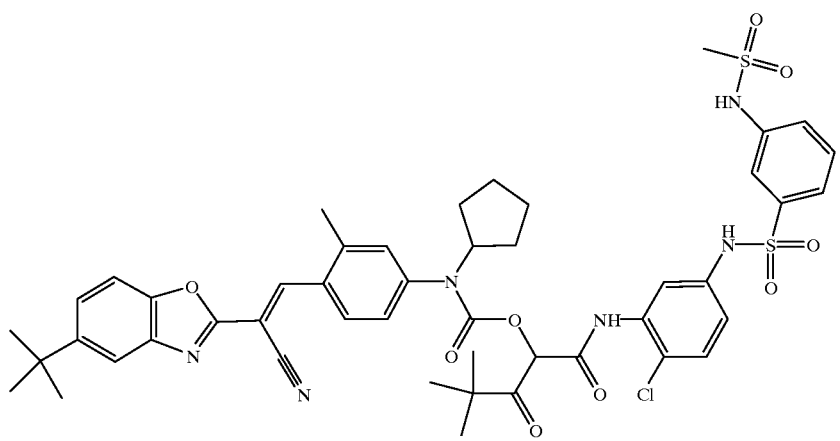
Inv-36
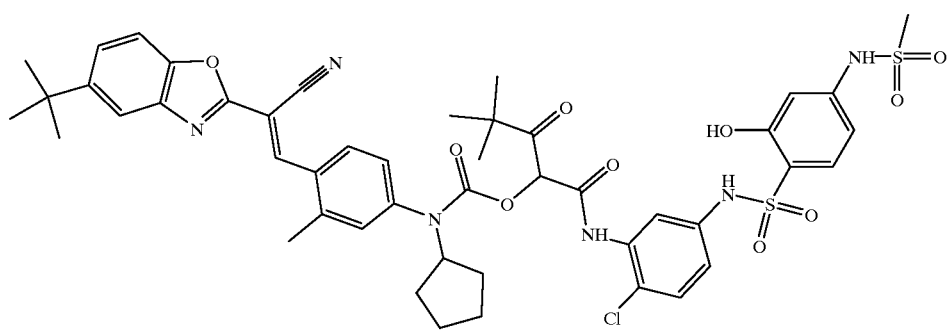

-continued
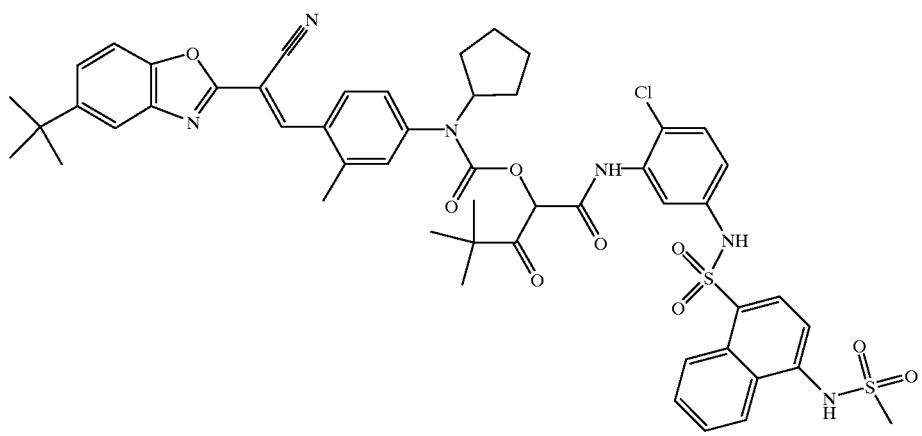
Inv-37
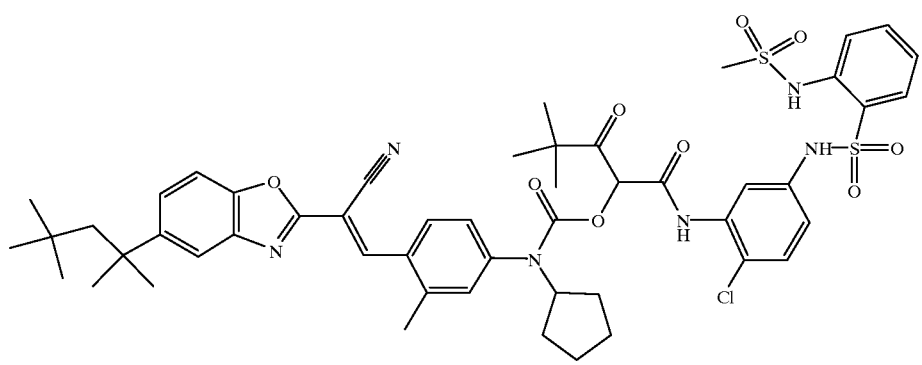
Inv-38
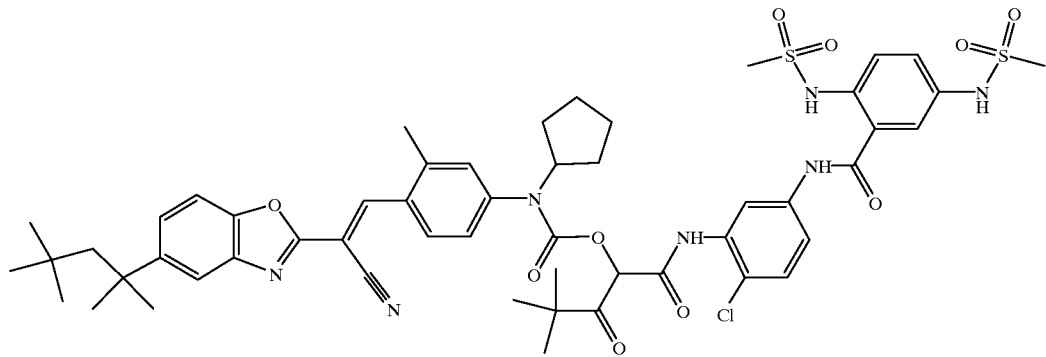
Inv-39
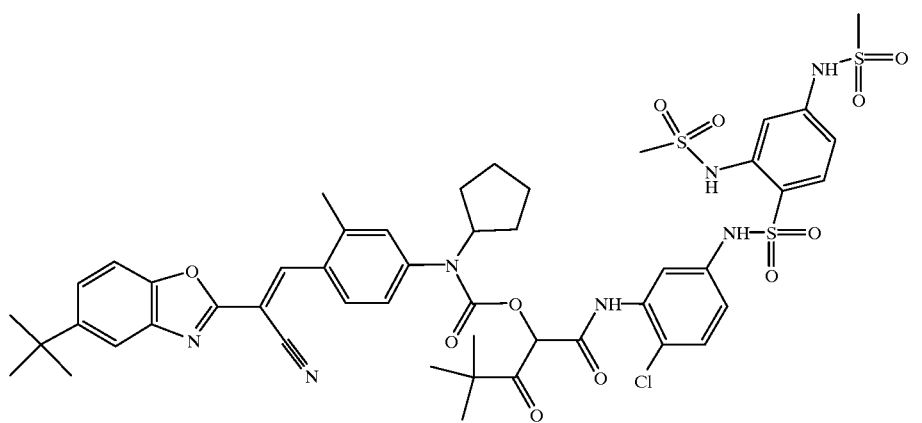
Inv-40

Inv-41
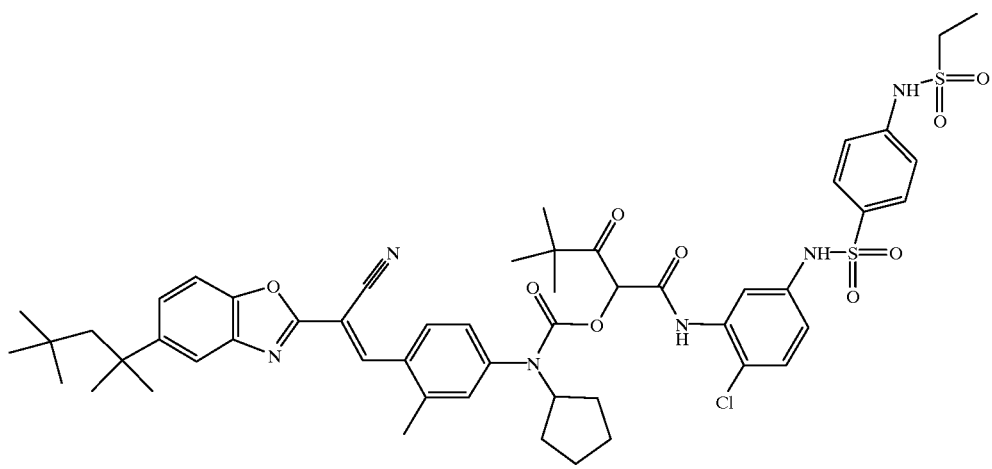
Inv-42
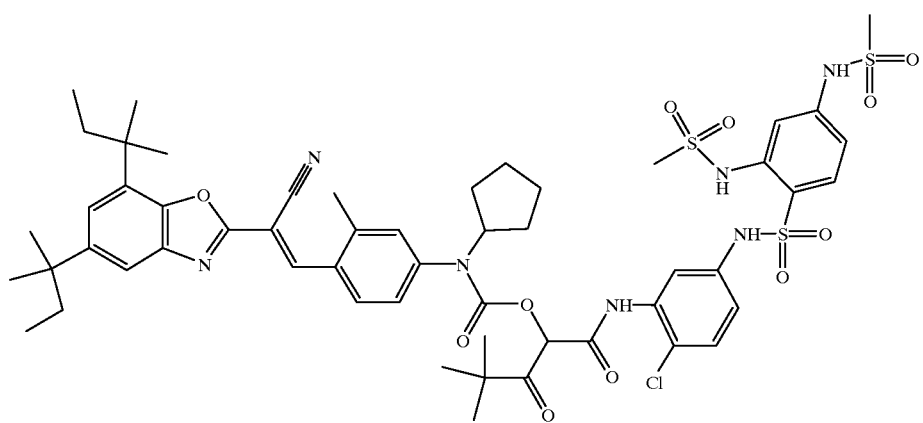
Inv-43
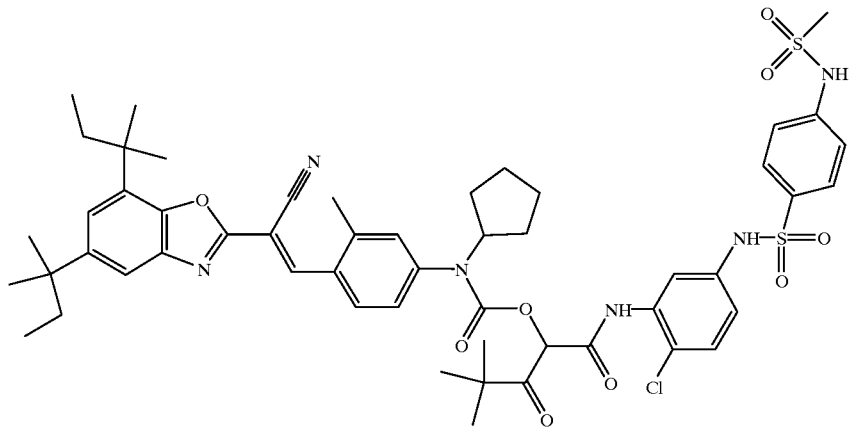

-continued
Inv-44
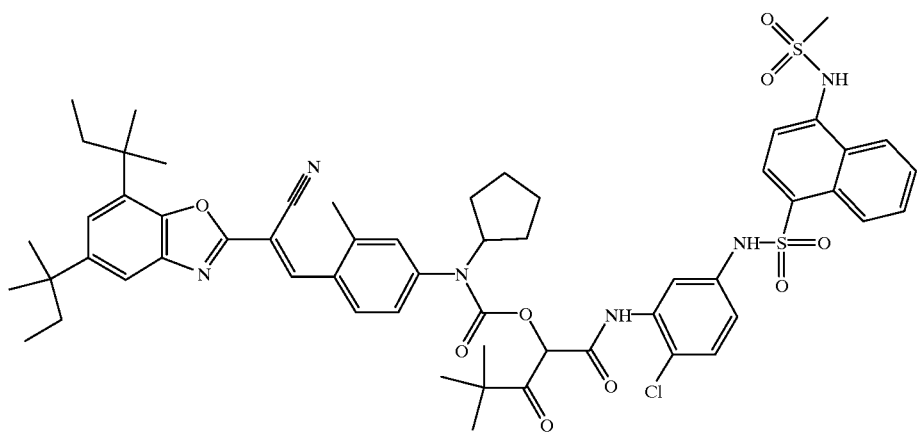
Inv-45
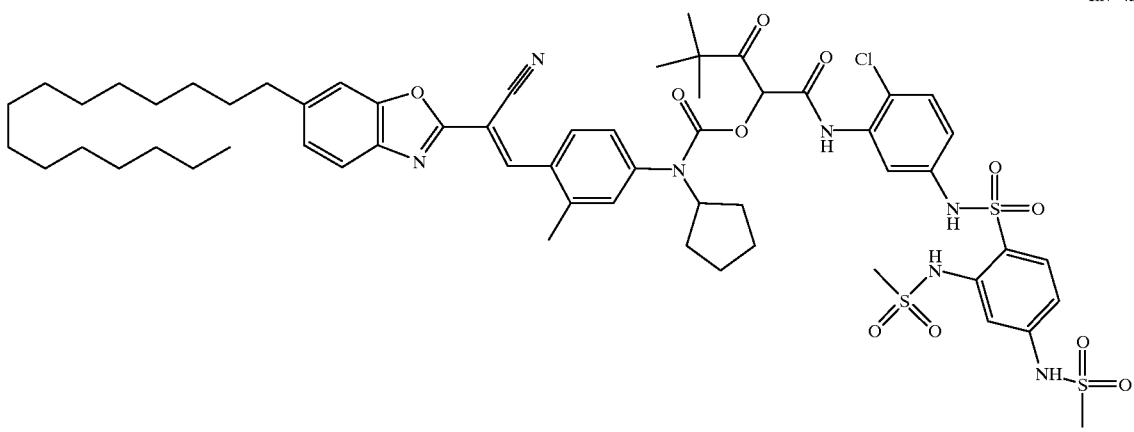
Inv-46
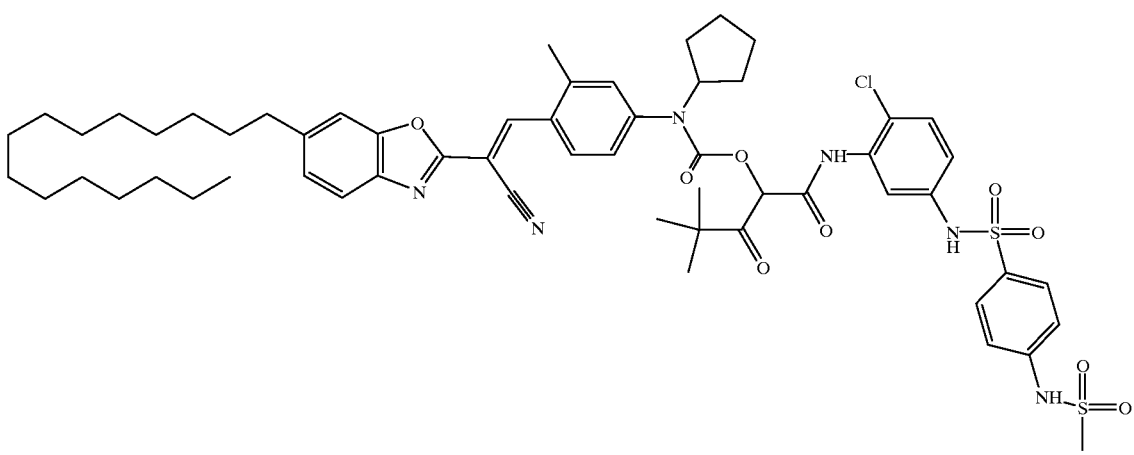

Inv-47
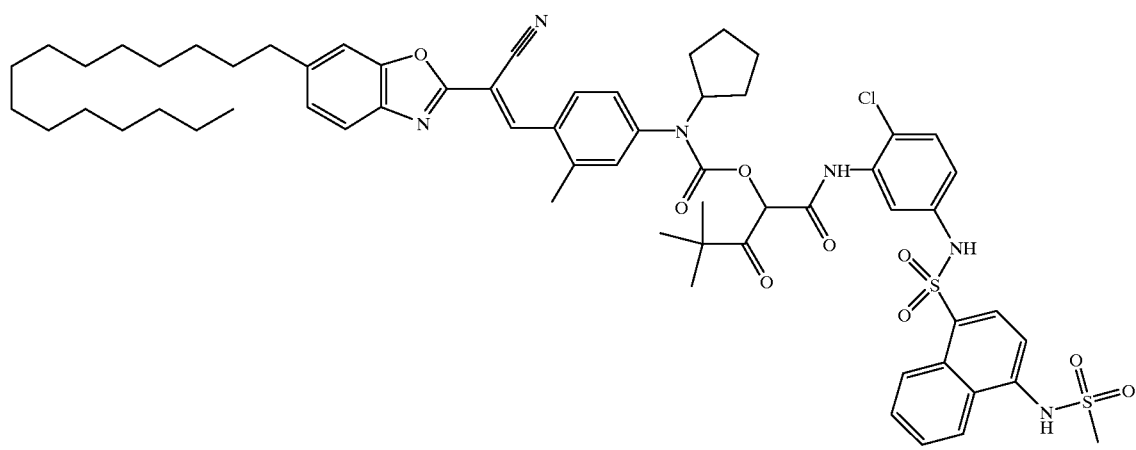
Inv-48
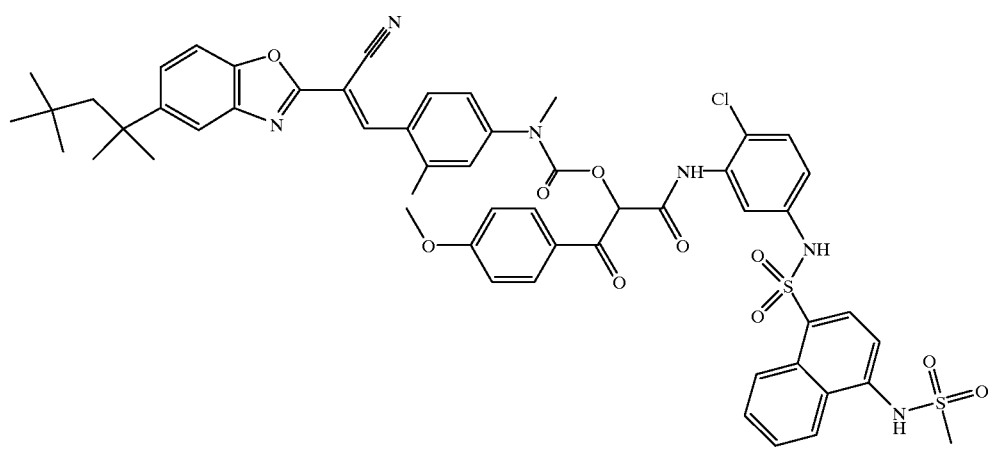
Inv-49
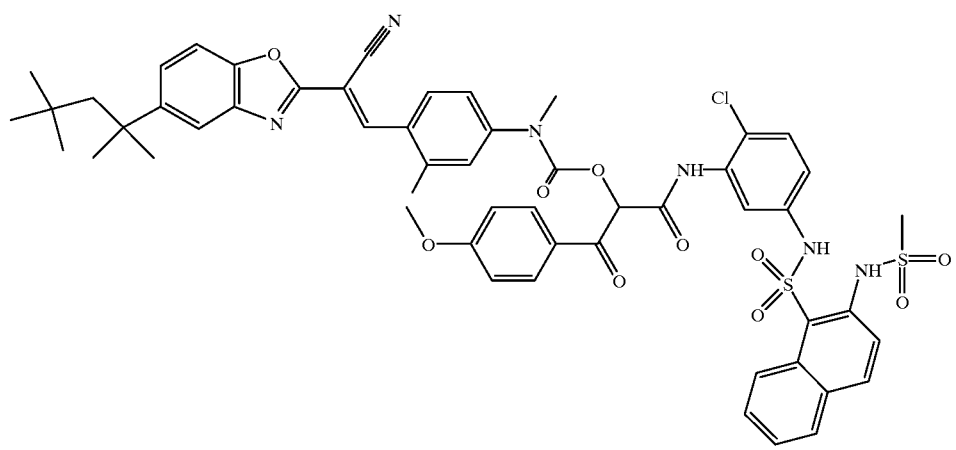

Inv-50
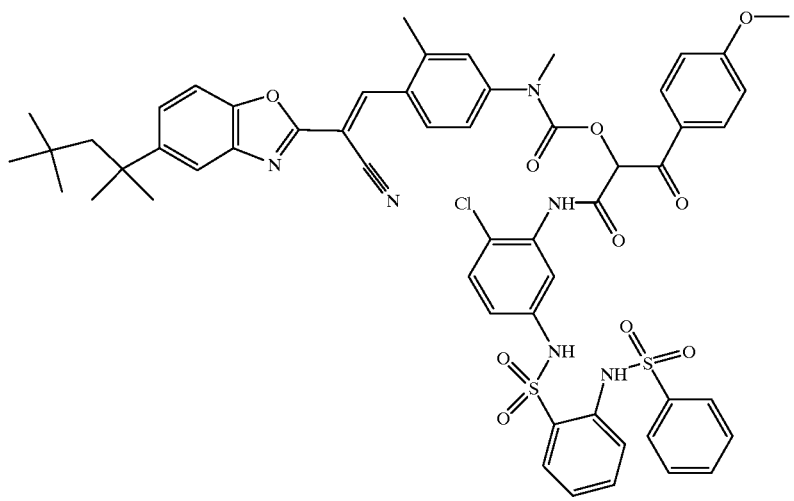
Inv-51
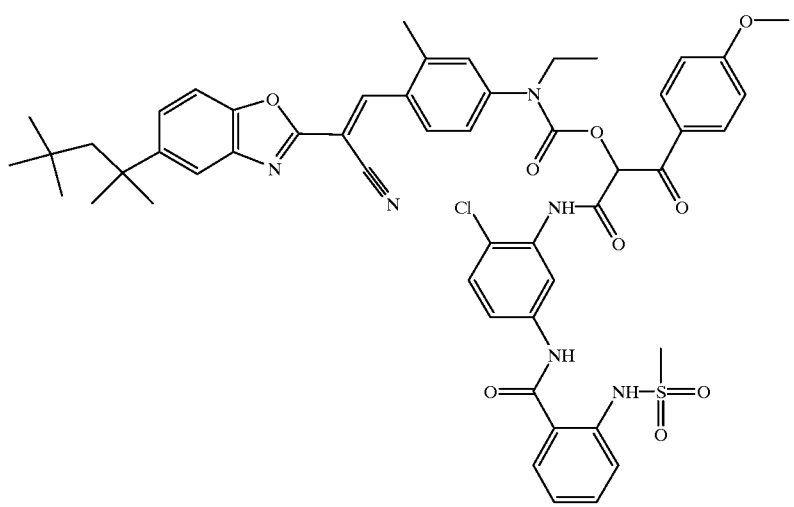
Inv-52
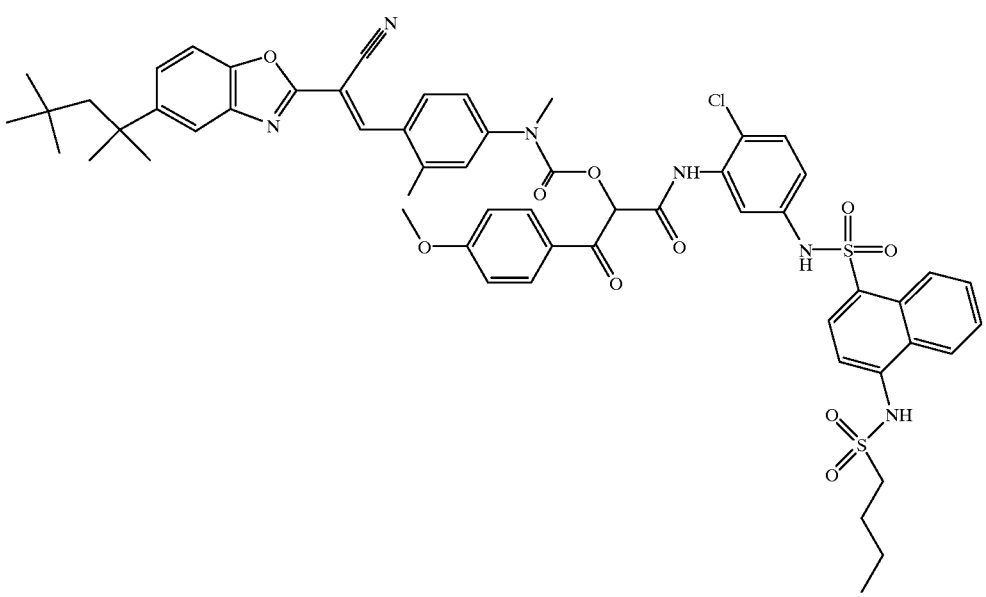

-continued
Inv-53
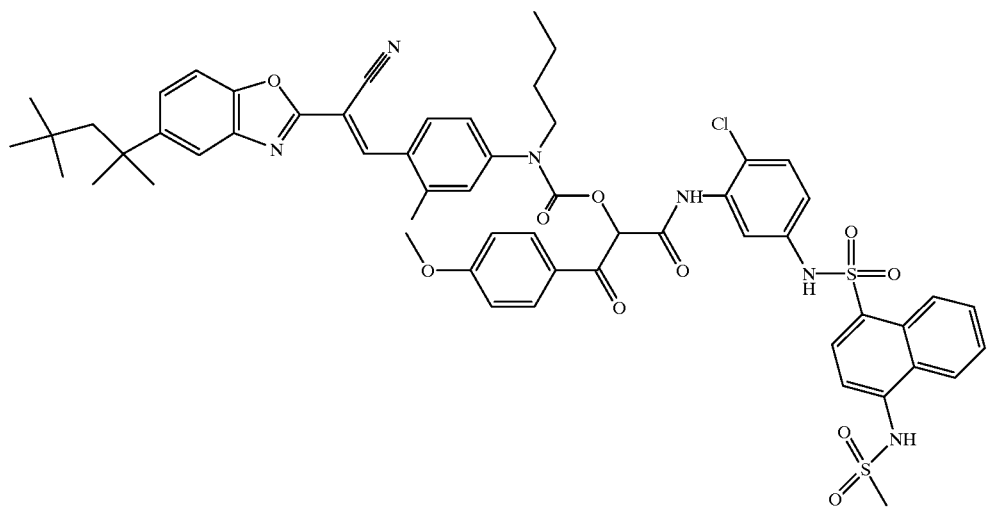
Inv-54
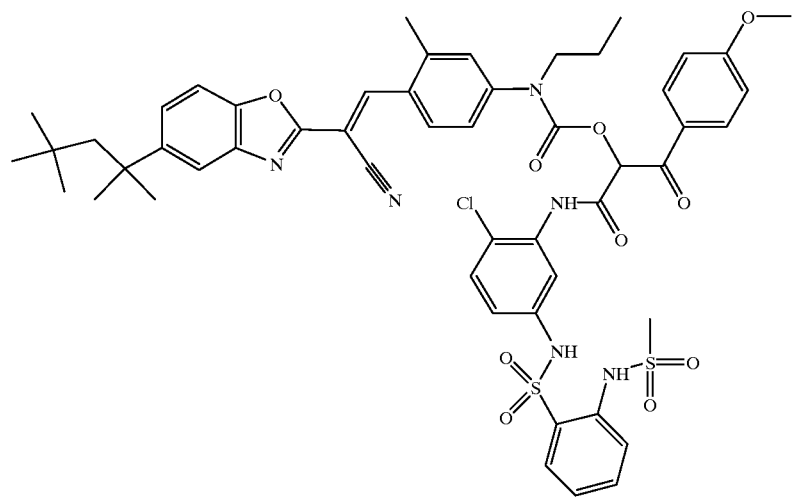
Inv-55
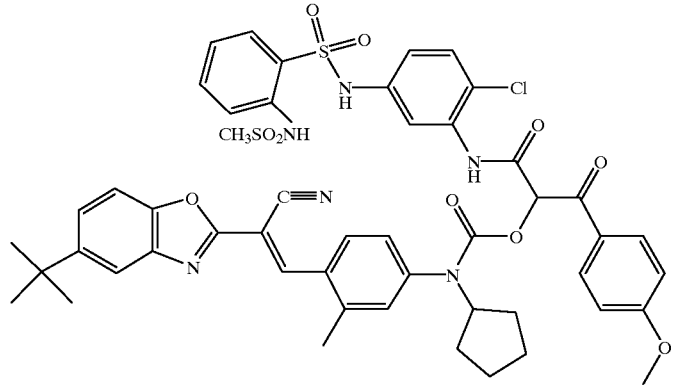

Inv-56
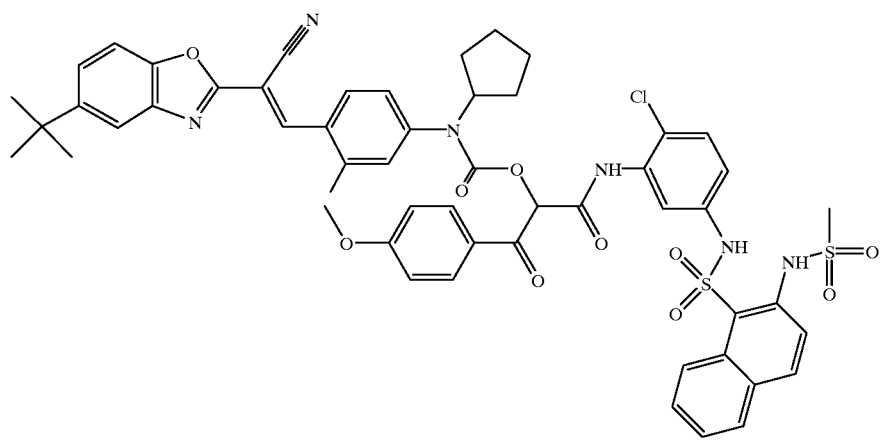
Inv-57
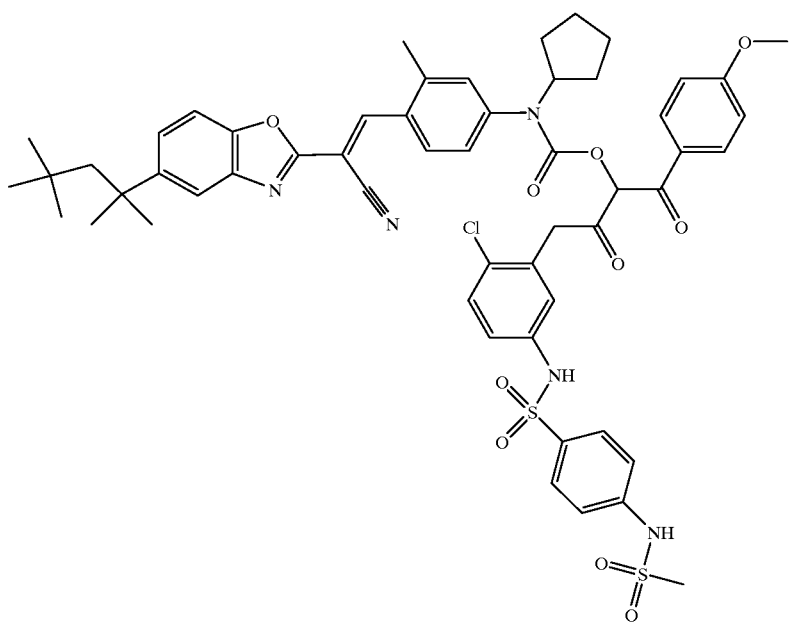
Inv-58
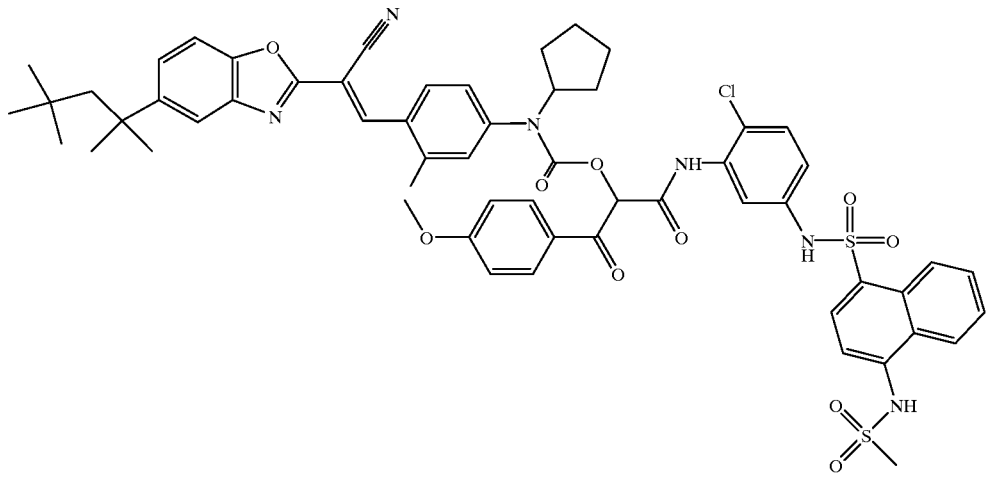

Inv-59
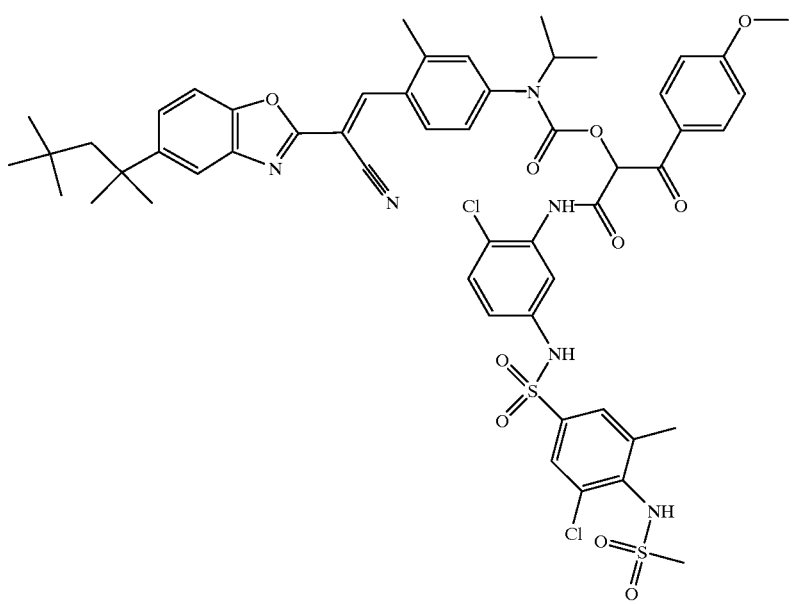
Inv-60
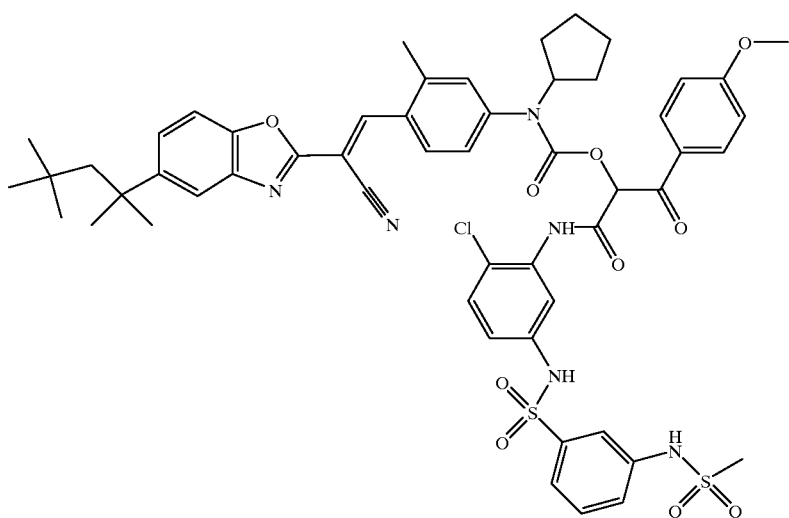

Inv-61
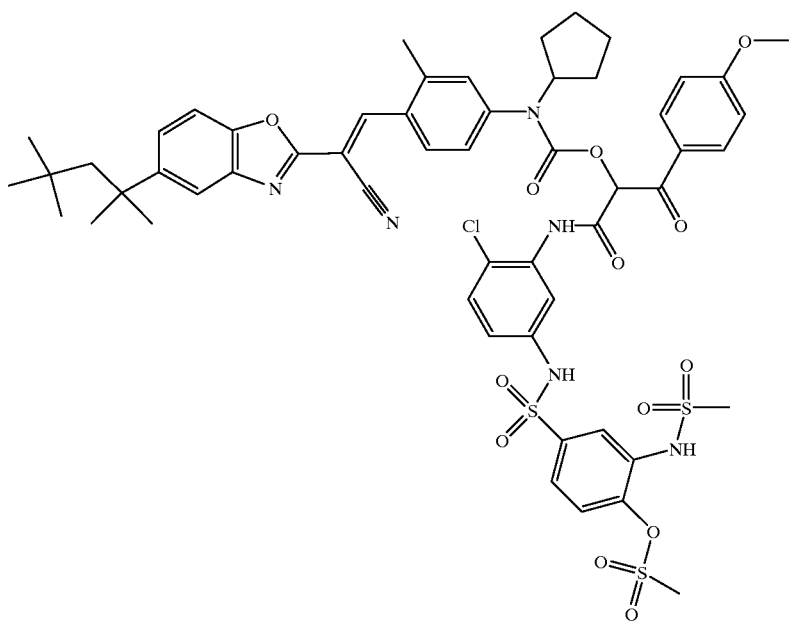
Inv-62
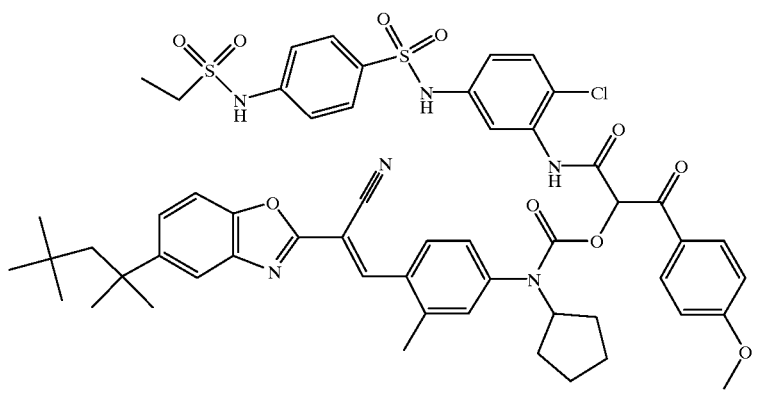
Inv-63
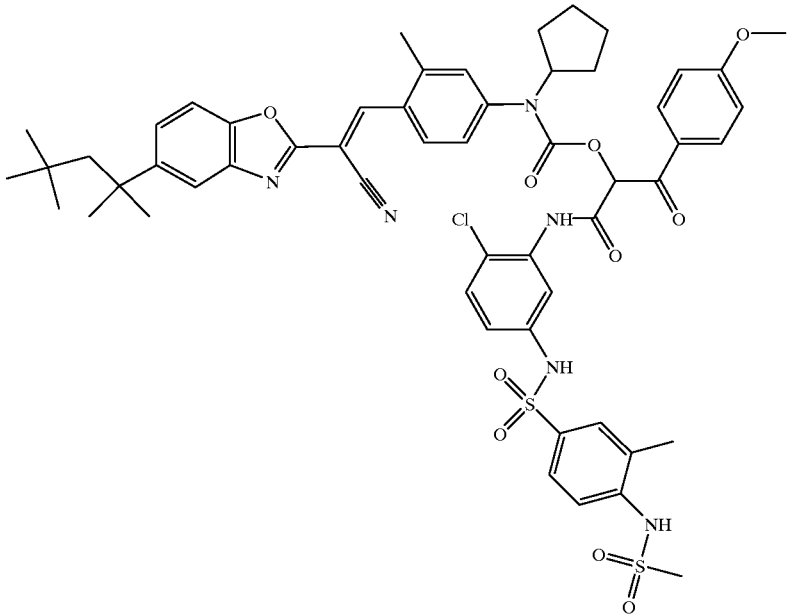

-continued
Inv-64
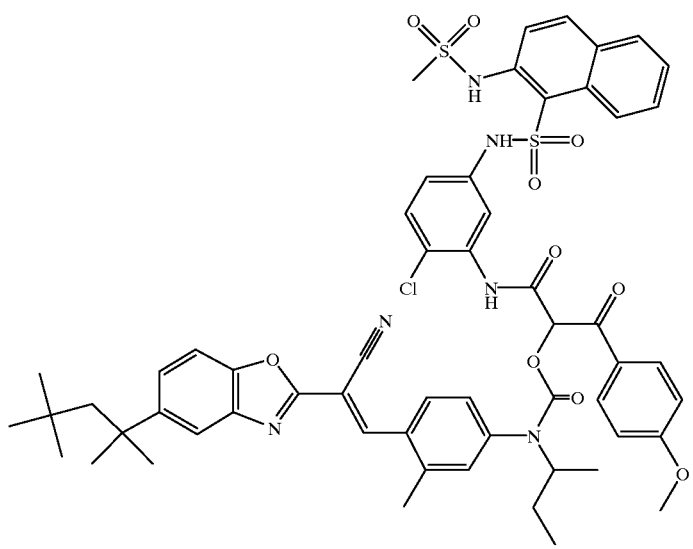
Inv-65
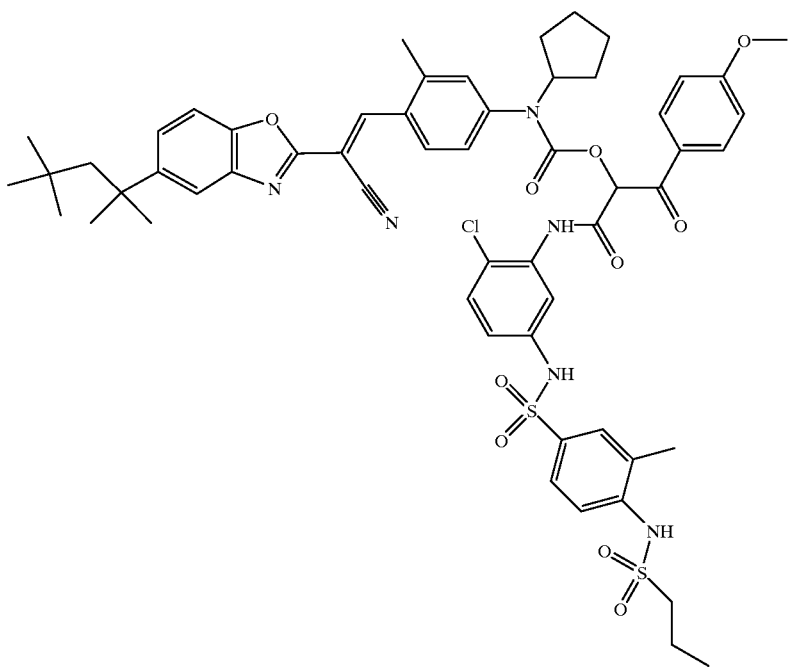
Inv-66
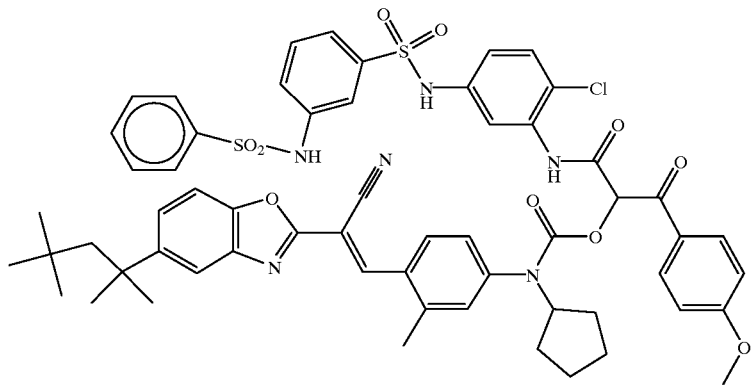

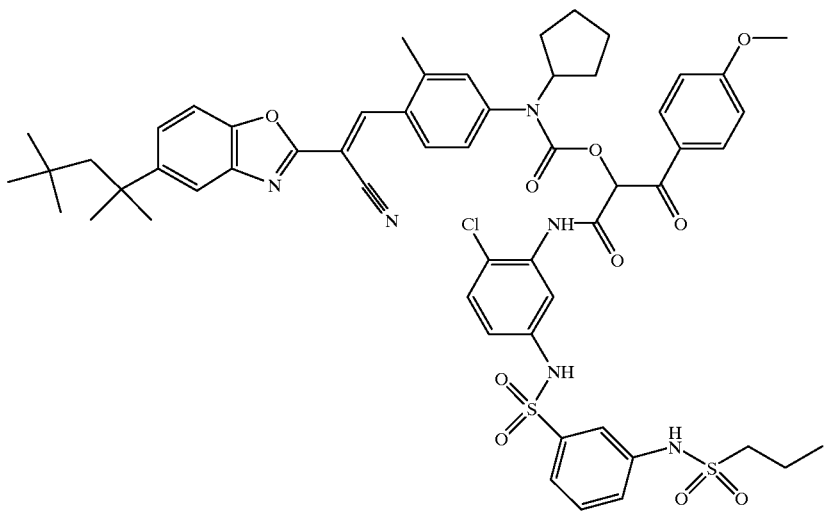

Inv-67

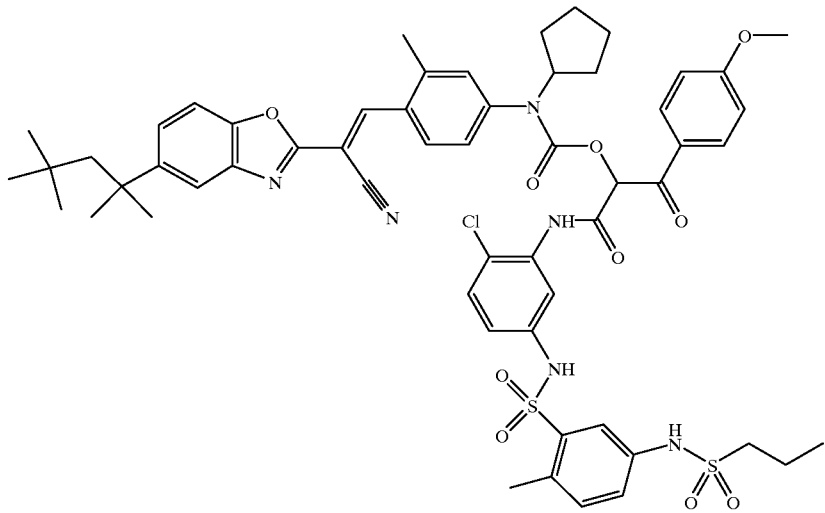

Inv-68

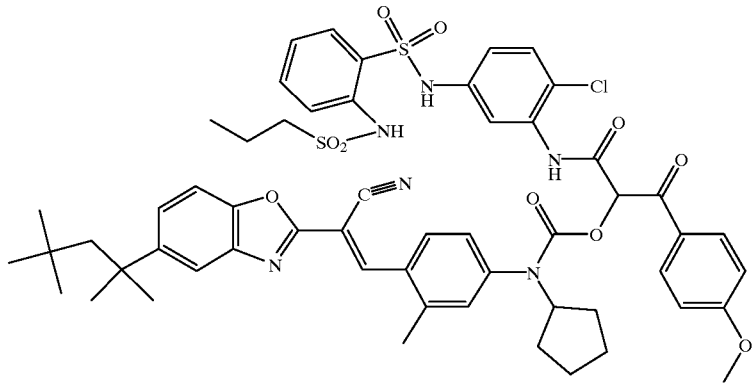

Inv-69

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamnido; sulfonarnido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

In addition to HDY couplers, other couplers may be used in the photographic element. Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766, and in UK. Patents and published application Nos. 1,466,728, 1,531,927, 1,533,039, 2,006, 755A and 2,017,704A, the disclosures of which are incorporated herein by reference.

Image dye-formning couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323; EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers in addition to HDY couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632,345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions using no permanent coupler solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

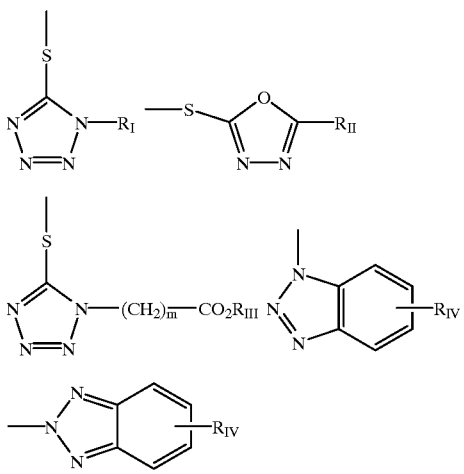

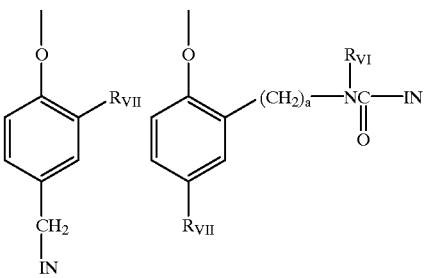

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R^I$ and —$SR_I$—; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

wherein IN is the inhibitor moiety, $R_{VII}$ is selected from the group consisting of nitro, cyano, alkylsulfonyl; sulfamoyl; and sulfonamido groups; a is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

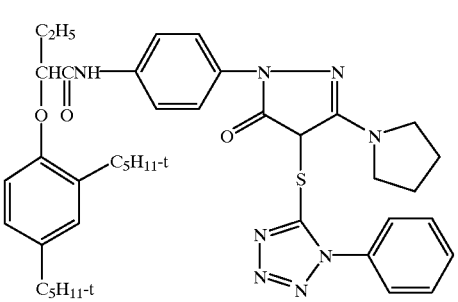

D1

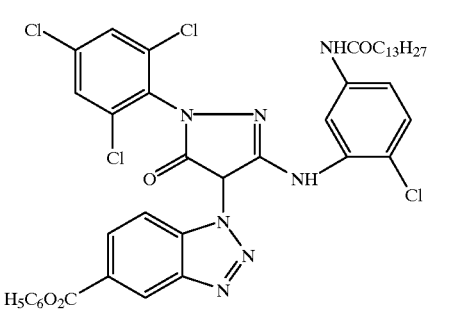

D2

-continued
D3
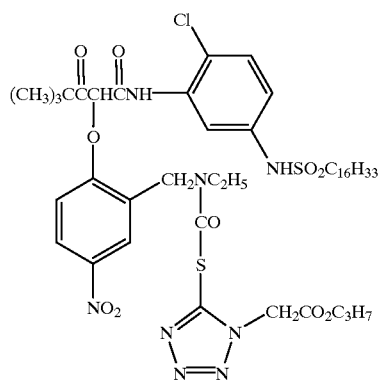
D4
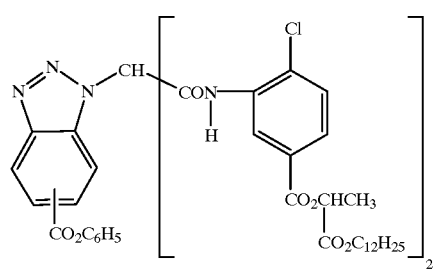
D5
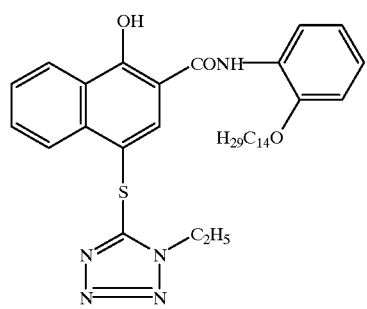
D6
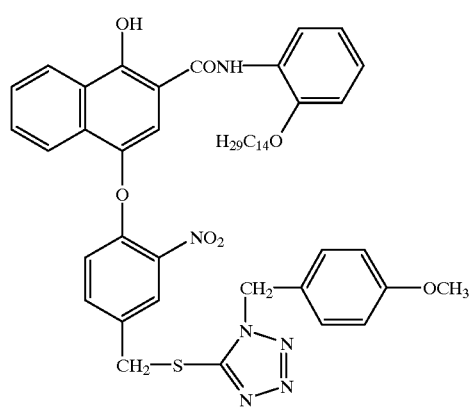
-continued
D7
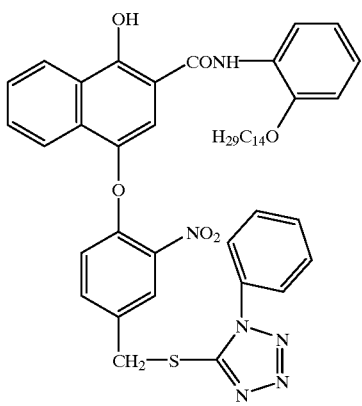
D8
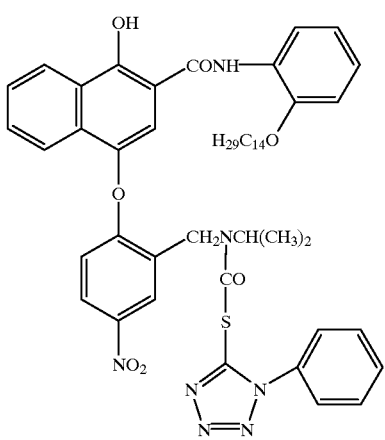
D9
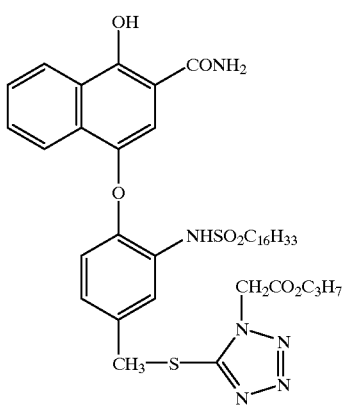

-continued

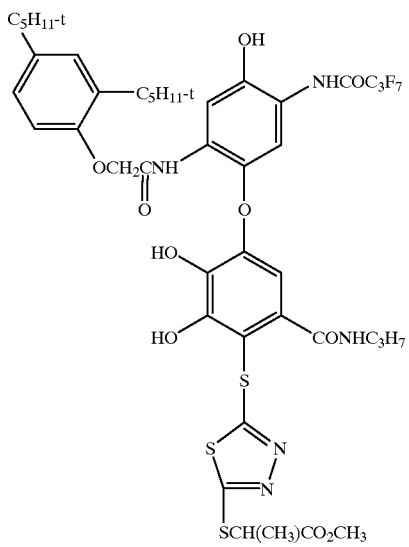

D10

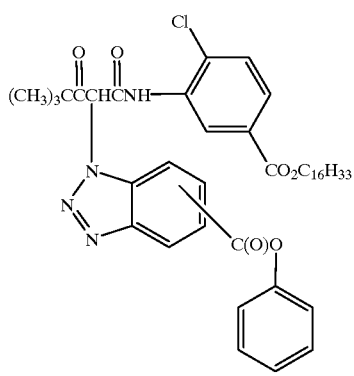

D11

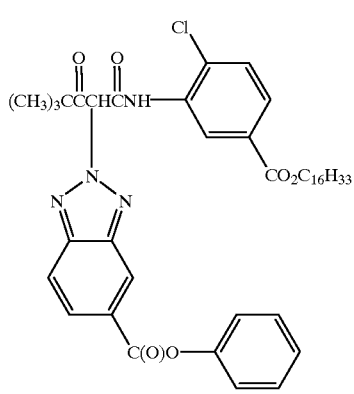

D12

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided by its thickness (t). Tabular grain emulsions are those in which the tabular grains account for at least 50 percent (preferably at least 70 percent and optimally at least 90 percent) of the total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111} or {100} crystal planes. The mean ECD of tabular grain emulsions rarely exceeds 10 micrometers and more typically is less than 5 micrometers.

In their most widely used form tabular grain emulsions are high bromide {111} tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435,501; 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061,609, Tsaur et al U.S. Pat. Nos. 5,147,771, '772, '773, 5,171,659 and 5,252,453, Black et al U.S. Pat. Nos. 5,219,720 and 5,334,495, Delton U.S. Pat. Nos. 5,310,644, 5,372,927 and 5,460,934, Wen U.S. Pat. No. 5,470,698, Fenton et al U.S. Pat. No. 5,476,760, Eshelman et al U.S. Pat. Nos. 5,612,175 and 5,614,359, and Irving et al U.S. Pat. No. 5,667,954.

Ultrathin high bromide {111} tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111} tabular grain emulsions are illustrated by Wey U.S. Pat. No. 4,399,215, Wey et al U.S. Pat. No. 4,414,306, Maskasky U.S. Pat. Nos. 4,400,463, 4,713,323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111} tabular grain emulsions are illustrated by Maskasky U.S. Pat. Nos. 5,271,858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320,938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and are sold packaged with instructions to process in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3' 15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold packaged with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal elements are typically sold packaged with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patents and other publications referred to in this specification are incorporated herein by reference.

Synthesis Example—Inv-5
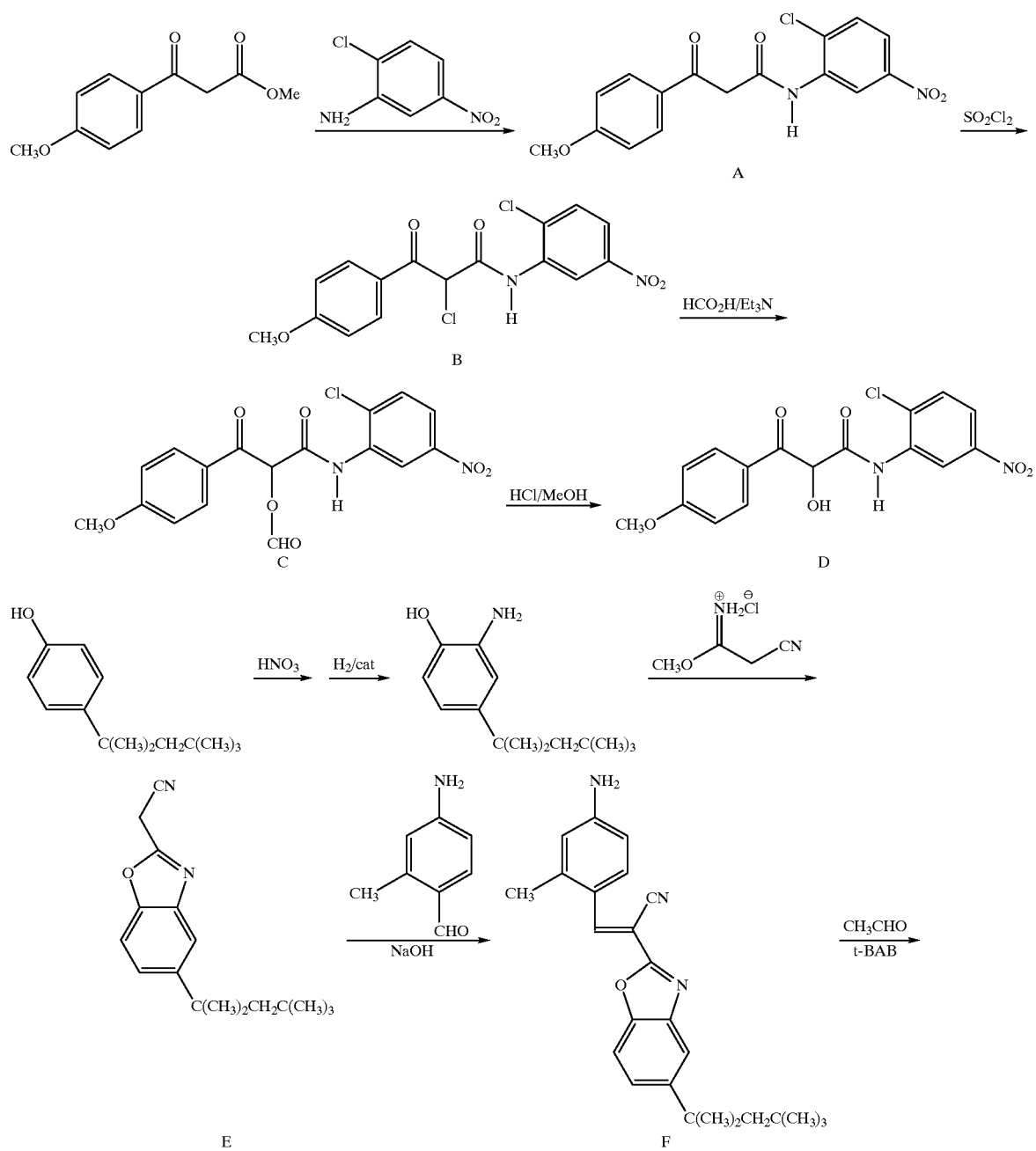

-continued
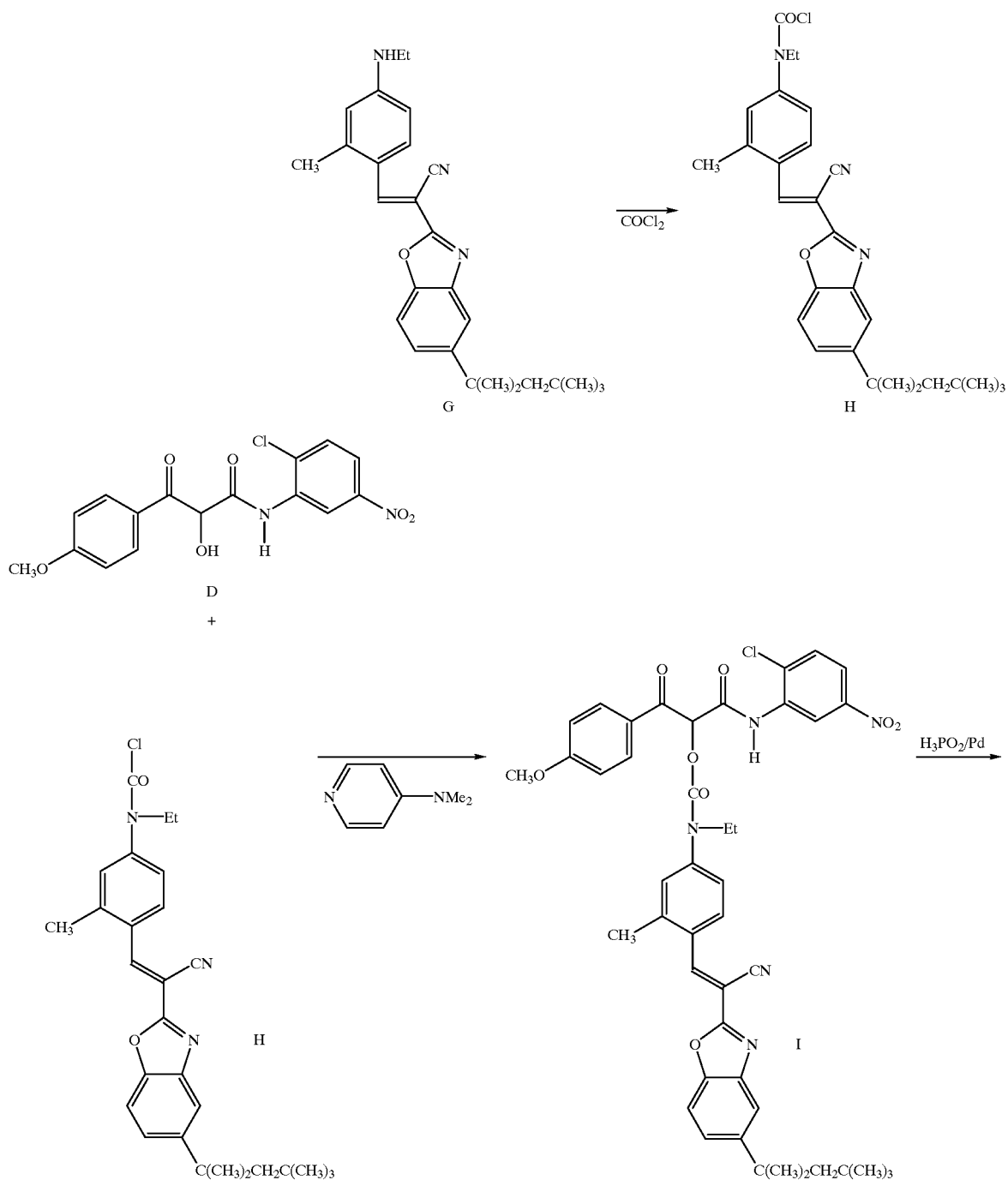

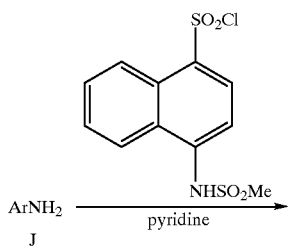
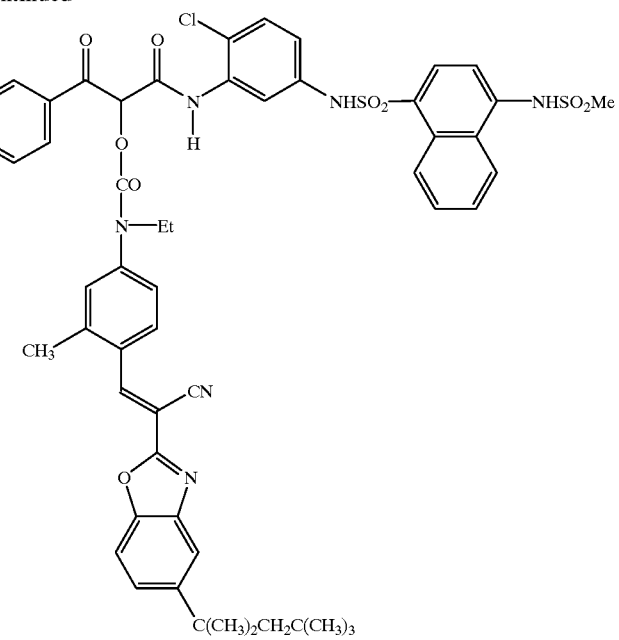

A mixture of methyl-(4-methoxybenzoyl)acetate (97 g, 0.47 mole), 2-chloro-5-nitroaniline (72 g, 0.42 mole), and 500 ml of xylene was heated under reflux and a slow stream of nitrogen for 6 hr. The mixture was allowed to cool to rt and stirred overnight. The crystalline product which formed was filtered off, washed with ether, and dried to 124 g (85%) of coupler intermediate A.

Coupler intermediate A (34.9 g, 0.1 mole), 300 ml of dichloromethane, and 8.1 ml of sulfuryl chloride were mixed, stirred vigorously, and heated to reflux momentarily. The mixture was then stirred at room temperature for 2 hours while the solid dissolved as chlorination proceeded. The mixture was concentrated at reduced pressure to a solid which was slurried in ether, filtered, and dried to yield 36.6 g (95%) of chloro coupler intermediate B.

Triethylamine (40.5 ml) and formic acid (96%, 11 ml) were mixed with 90 ml of acetonitrile and cooled to room temperature. The mixture was stirred while chloro coupler intermediate B (36.6 g, 0.0955 mole) was added. After 1 hour the mixture was diluted with 120 ml of 1N HCl and stirred while a precipitate formed. The solid was filtered off, washed with water, and air dried to 36 g of crude product. After crystallization from methanol/tetrahydrofuran, 28.9 g (77%) of pure coupler intermediate C was obtained.

Coupler intermediate C (28.9 g, 0.073 mole) was dissolved in 120 ml of tetrahydrofaran. Methanol (120 ml) and 12 ml of conc. HCl were added before raising the temperature of the mixture momentarily to 40° with a warm water bath. The mixture was then stirred at room temperature and seeded with product crystals after 5 min. Water (15 ml) was added after 20 min and again after 1 hour (50 ml). The thick suspension was filtered after 1.25 hr, washed with water, a little 50% aqueous methanol, and then ether before drying to 22.5 g (84%) of hydroxy coupler intermediate D.

Nitric acid (10.6 ml of 90% acid, density=1.57, 0.26 mole) was added dropwise over about 10 min to a solution of 4-t-octylphenol (50 g, 0.24 mole) in 500 ml of acetic acid kept at room tempersature or below by means of an ice bath. The mixture was stirred for another 10 min after addition was complete and then diluted with 2.5 l of heptane. The heptane solution was washed 5 times with 1-1 portions of cold water and then once with 500 ml of brine. The heptane solution was then passed through about 2 l of silica gel in a large filter funnel. Additional heptane containing 2 to 5% of ethyl acetate was used to elute the 2-nitro-4-t-octylphenol product as a yellow oil (49.8 g, 82%).

This oily phenol (182 g, 0.724 mole) was combined with 1.2 l of isopropyl alcohol and 12 g of 5% Pd/C in a 5 l flask fitted with uncooled condenser, mechanical stirrer, and 50° water bath. Ammonium formate (182 g, 2.9 mole) was added portionwise over about 15 min at such a rate as to avoid excessive foaming. Heating at 50° was continued for an additional 30 min before cooling to room temperature. Ethyl acetate (1.5 l) was added to dissolve the aminophenol before filtering the solution to remove catalyst. The filtrate was washed twice with salt water (700 ml water plus 300 ml brine) and then once with 300 ml of brine. After drying over $MgSO_4$ and concentrating to an oil, the product (2-amino-4-t-octylphenol, 154 g, 96%) was crystallized from 1.5 l of heptane.

A mixture of malononitrile (39.6 g, 0.6 mole), methanol (48 ml, 1.2 mole) and 180 ml of methyl formate was cooled to about 15°. Thionyl chloride (33.6 ml, 0.46 mole) was added dropwise to the vigorously stirred solution over about 45 min while keeping the temperature at 15–20°. The mixture was stirred for about 30 min more while a solid salt formed and then filtered. The solid was washed with methyl formate and then dried under a slow stream of nitrogen under vacuum to yield 57 g (69%) of hygroscopic solid methyl cyanoacetate-imino ester hydrochloride. This procedure was repeated a number of times and the combined product (194 g, 1.45 mole) was used immediately after drying by transferring to a 5-liter flask fitted with mechanical stirrer, heating mantle, and reflux condenser. Methanol (1.2 l) and 2-amino-4-t-octylphenol (160 g, 0.72 mole) were added before refluxing the mixture for 45 min. The mixture was cooled to room temperature and filtered. The filtrate was concentrated to a syrup, dissolved in 2 l of heptane, washed with 5×1 l portions of water, washed once with 300 ml of brine, dried over MgSO$_4$, and concentrated again to syrupy cyanomethyl benzoxazole intermediate E (155 g, 80%).

Reduction of 4-nitroxylene with sodium sulfide to 4-amino-2-methylbenzaldehyde is reported in the literature [David A. Burgess and Ian D. Rae, *Aust. J Chem.*, 1977, 30, 927–31; Lennart Florvall and Maj-Liz Persson, *Acta. Chemica. Scandinavica* B, 36 (1982) 141–146]. A homogeneous solution of sodium sulfide was prepared by mixing sodium sulfide nonahydrate (147 g, 0.615 mole), sodium hydroxide (53 g, 1.33 mole), elemental sulfur powder (27.8 g, 0.87 mole), and 950 ml of hot (55°) water in a 3-l flask equipped with mechanical stirrer, reflux condenser, and heating mantle. A solution of 4-nitro-o-xylene (100.7 g, 0.67 mole) in 550 ml of ethanol was added before refluxing the mixture for 1.5 hr. The mixture of crude aldehyde was cooled to room temperature and treated with a solution of cyanomethyl benzoxazole intermediate E (150 g, 0.56 mole) in 190 ml of tetrahydrofuran plus 95 ml of ethanol. This mixture was stirred at room temperature for 2 hours while methine dye product precipitated. The dye was filtered off, washed with 500 ml of 50% aqueous methanol, washed with 500 ml of 80% methanol-water, and dried to yield 130 g (60%) of methine dye intermediate F.

Methine dye intermediate F (58.1 g, 0.15 mole) was dissolved in 150 ml of dimethylformamide and cooled to 0°. The solution was stirred while adding 16.8 ml of acetaldehyde followed by a solution of t-butylamino borane (t-BAB, 7.8 g, 0.09 mole) in 150 ml of acetic acid. Alkylated dye began to precipitate after a few minutes so the mixture was warmed to room temperature, stirred for 30 min, and then diluted with 100 ml of 50% aqueous methanol. The dye was filtered off, washed with methanol, dissolved in dichloromethane, concentrated, and re-precipitated with methanol to yield pure methine dye intermediate G (46.6 g, 75%).

Methine dye intermediate G (46.6 g, 0.112 mole) was dissolved in a solution of 2,6-lutidine (14 ml, 0.12 mole) and 300 ml of dichloromethane. The mixture was stirred vigorously at room temperature while adding phosgene (60 ml of 2M solution in toluene, 0.12 mole). After 30 min the solution was washed with 1N HCl, dried over MgSO$_4$, and passed though a small pad of silica gel to remove polar impurities using 10% ether in dichloromethane to elute the product dye carbamyl chloride intermediate H (crystallized from heptane, 49.6 g, 93%).

Hydroxy coupler intermediate D (8 g, 0.022 mole), methine dye carbamyl chloride intermediate H (10.5 g, 0.022 mole), dimethylaminopyridine (3.2 g, 0.0264 mole), 3A molecular sieves (22 g), and 60 ml of dichloromethane were stirred under nitrogen atmosphere for 30 min. After washing the mixture with 1N HCl and concentrating to a syrup, the crude product was chromatographed on 400 g of silica gel using 2–10% acetonitrile in toluene as eluent. Nitro coupler intermediate I (6 g, 31%) was obtained as a crystalline solid from ether/heptane.

Nitro coupler intermediate I (5.08 g, 0.0063 mole) in 50 ml of toluene was reduced at 70° over 45 min by the addition of 700 mg of 5% Pd/C and 6.9 ml of 50% aqueous hypophosphorous acid. The mixture was filtered to remove catalyst, washed with 3:1 water:brine, dried over MgSO$_4$, and concentrated to gummy amino coupler intermediate J which crystallized from ether/heptane (4.3 g, 88%).

A suspension of 4-amino-1-naphthalene sulfonic acid (200 g, 0.897 mole) in 800 ml of pyridine was stirred mechanically while methanesulfonyl chloride (70 ml, 0.9 mole) was added slowly over about 10 min. The reaction warmed to about 60° as the solid dissolved and then slowly cooled to room temperature. The mixture was stirred overnight while a solid precipitated. After filtering and washing with 500 ml of ether, the solid was dried under a nitrogen stream to afford 211 g (62%) of 4-methanesulfonamido-1-naphthalene sulfonic acid pyridinium salt.

A suspension of the pyridinium salt (211 g, 0.555 mole), sodium sulfate (79 g, 0.555 mole), 1.1 l of acetonitrile, and phosphoryl chloride (201 ml, 2.2 mole) was stirred at room temperature for 16 hours. The reaction mixture was diluted with 2.5 l of ethyl acetate and washed 5 times with 1 l of ice water and then once with 500 ml of brine. The washed solution was dried over MgSO$_4$ and concentrated to a solid which was slurried in about a liter of heptane and filtered. The filter cake was dried under a stream of nitrogen to yield 158 g (89%) of 4-methanesulfonamido-1-naphthalene sulfonyl chloride.

Amino coupler intermediate J (3.88 g, 0.005 mole) was dissolved in a mixture of 0.8 ml of pyridine, 5 ml of isopropanol, and 5 ml of tetrahydrofuran before adding 4-methanesulfonamido-1-naphthalene sulfonyl chloride (1.92 g, 0.006 mole) and stirring at rt for 30 min. The mixture was diluted with ethyl acetate and washed with 1N HCl and then brine. After drying over MgSO$_4$ and passing though a short pad of silica gel, the crude product was crystallized from ether/heptane to yield 4.3 g (81%) of solubilized coupler Inv-5.

In the following examples, the pKa values were determined by standard procedures using spectrophotometric titration of the compounds of interest. The spectrophotometric technique involves measuring the absorption spectra of the compound of interest in a range of buffer solutions. The absorption data (optical densities, ODobsd) can then be used to determine the corresponding pKa value(s) according to eq 1–3

$$\text{ODobsd} = \text{OD}_{HnA} + \text{OD}_{Hn-1A} + \quad (1)$$

$$= b[\text{HnA}]\epsilon_{HnA} + b[\text{Hn-1A}]\epsilon_{Hn-1A} \quad (2)$$

$$= b[\text{total}]f_{HnA}\epsilon_{HnA} + b[\text{total}]f_{Hn-1A}\epsilon_{Hn-1A} \quad (3)$$

b=optical path length
[total]=total concentration of compound, i.e., sum of all species
$\epsilon$=extinction coefficient of a given species
f=fraction of a given species
Typically, the experimental constants (b and [total]) are combined with the extinction coefficient ($\epsilon$) and expressed as the maximum optical density (OD$_{max}$) for a given species. Eq 3 then becomes, $$= \text{ODmax}_{HnA}f_{HnA} + \text{ODmax}_{Hn-1A}f_{Hn-1A} \quad (4)$$

The fraction of a given species (f) is a function of the pH and pKa values.
For example, for a system with one titratable proton eq 5–6, $$f_{HA} = (1+\text{Ka/H})^{\wedge}(-1) \quad (5)$$

$$f_A = (1+\text{H/Ka})^{\wedge}(-1) \quad (6)$$

where Ka=10$^{\wedge}$(-pKa)
and H=10$^{\wedge}$(-pH)
Thus, the pKa and ODmax values can be determined from a set of XY pair data (pH, ODobsd) using a non linear least squares fit.

This technique relies on a difference in extinction coefficient between the species of interest at a given wavelength.

This can be seen by inspection as a change in the absorption spectrum over a given pH range. In addition to this macroscopic data, (the experimental pKa values), the spectrophotometric technique can also provide microscopic information, i.e., information about the relationship between the individual titratable groups and the pKa values. In this manner, a pKa value may be attributed to titration of a particular group in a molecule, e.g., a solubilizing group.

The absorption spectra over a range of pH values and pKa values for the model sulfonamides such as Comp-11 and Comp-8 (defined for the examples hereinafter) as well as the coupler Comp-12 may be plotted. In model sulfonamide Comp-11 (pK 6.65), the optical density change resulting from ionization of the sulfonamide which is in conjugation with the naphthalene group may be pinpointed. Model sulfonamide Comp-8 comprises the entire solubilizing group $pK_1$ 7.03, $pK_2$ 10.00). The spectrophotometric titration of this compound exhibits an OD change at the lower pH range similar to that observed for Comp-11, followed by an OD change at the higher pH values which may be attributed to ionization of the second sulfonamide (in conjugation with the phenyl ring). Finally, in the spectrophotometric titration of the coupler Comp-12, the ionization of both sulfonamides in the solubilizing group as well as ionization of the coupling site $pK_1$ 6.85, $pK_2$ 9.85, $pK_3$ 10.84) can be seen.

In practice, a stock solution of the appropriate compound $(1 \times 10^{-4}$ M) and Triton X-100 (1.2%) in water was prepared. The Triton X-100 (CAS Registry No. [9002-93-1], polyoxyethylene(10) isooctylcyclohexyl ether) was obtained from Aldrich Chemical Co. and used as received. To 1.50 mL of the appropriate phosphate buffer ($\mu$=0.75) were added 1.50 mL of the stock solution. The solution was agitated to ensure adequate mixing, and its absorption spectrum and pH were measured. A non linear least squares method was then used to fit the data to a one, two, or three pKa value model as appropriate.

PHOTOGRAPHIC EXAMPLES

Example 1

Test samples were prepared, processed and tested as follows.
Single Layer Examples:
The formats for single layer samples were as follows (amounts in g/m2 unless otherwise specified).
SINGLE LAYER FORMATS:

Format 1:

| | |
|---|---|
| Layer 1 | Gelatin 1.08 g/m² |
| | Hardener (1,1'-{oxybis(methylenesulfonyl}bis-ethene |
| | (2% of total gelatin) |
| | Spreading Agent (Saponin 1% of total volume). |
| Layer 2 | Gelatin (2.42 g/m²) |
| | Emulsion (2.15 g/m² Ag, 2.5 $\mu$mmean size, 9 mole % |
| | Iodide, silver iodobromide emulsion. |
| | Image coupler coated at 0.4 mmole/m² or 0.2 mmole/m². |
| | Spreading Agent (Saponin 1% of total volume) |
| Remjet Film Base | |

Format 2:

| | |
|---|---|
| Layer 1 | Gelatin 1.08 g/m² |
| | Hardener (1,1'-{methylenebis(sulfonyl)}bis-ethene |
| | (2% of total gelatin) |
| | Spreading Agent (Saponin 1.5% of total volume). |
| Layer 2 | Gelatin (2.69 g/m²) |
| | Emulsion (0.40 g/m² Ag, 1.3 × 0.2$\mu$, |
| | 4 mole % Iodide, silver |
| | iodobromide tabular grain emulsion. |
| | Image coupler coated at 0.4 mmole/m² or 0.2 mmole/m². |
| | Spreading Agent (Saponin 1% of total volume) |
| Anti-halation layer on Film Base | Gelatin (2.44 g/m²) |
| | Black metallic silver (0.34 g/m²) |

Format 3:

| | |
|---|---|
| Layer 1 | Gelatin 1.08 g/m² |
| | Hardener (1,1'-{methylenebis(sulfonyl)}bis-ethene |
| | (2% of total gelatin) |
| | Spreading Agent (Saponin 1.5% of total volume). |
| Layer 2 | Gelatin (2.69 g/m²) |
| | Emulsion (0.65 g/m² Ag, 3.02 × 0.14 $\mu$m, |
| | 4.1 mole % Iodide, silver iodobromide tabular |
| | grain emulsion. |
| | Image coupler coated at 0.54 mmole/m² or 0.27 mmole/m². |
| | Spreading Agent (Saponin 1% of total volume) |
| Anti-halation layer on Film Base | Gelatin (2.44 g/m²) |
| | Black metallic silver (0.34 g/m²) |

Format 4:

| | |
|---|---|
| Layer 1 | Gelatin 2.7 g/m² |
| | Hardener (1,1'-{oxybis(methylenesulfonyl}bis-ethene |
| | (1.75% of total gelatin) |
| | Spreading Agent (Saponin 1.5% of total volume). |
| Layer 2 | Gelatin (3.77 g/m²) |
| | Emulsion (0.76 g/m² Ag, 0.7 $\mu$m mean size, |
| | 3.5 mole % Iodide, undyed, polymorphic silver |
| | iodobromide emulsion. Image coupler coated |
| | at 1.3 mmole/m² |

The image couplers were, typically, dispersed in di-n-butyl phthalate. Coated strips were exposed using a conventional step-wedge and processed using the Kodak Flexicolor C41 process.

Couplers were coated as follows:

Format 1: Comp-2 and Comp-3

Format 2: Comp-5 and Comp-6

Format 3: All other couplers

Format 4: Comp-1

In each case, the high dye-yield couplers were coated at the lower laydown of those given for the format.

The following comparative compounds were tested in various examples as indicated.

C-1
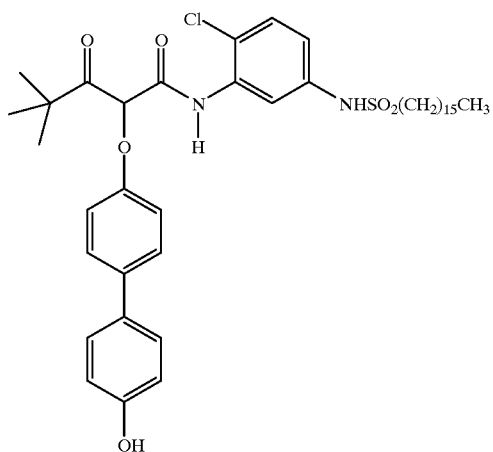
Comp-1
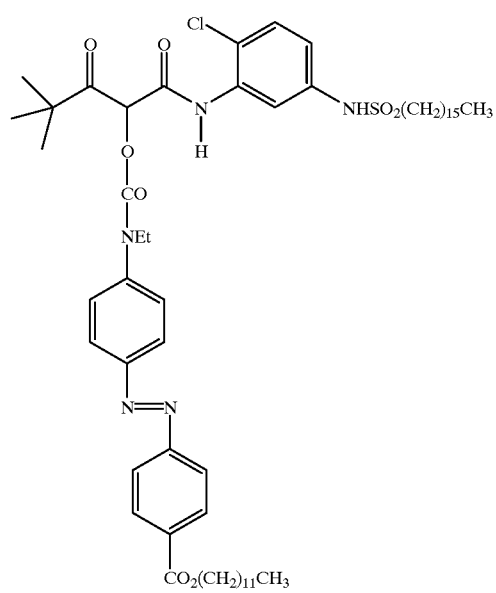
Comp-2
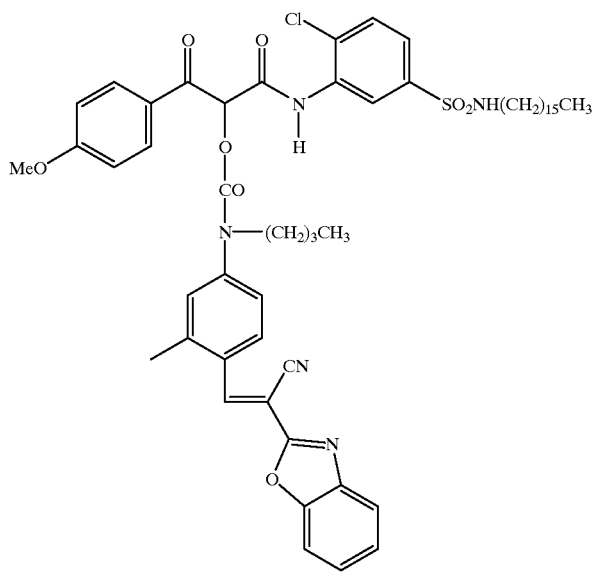

Comp-3
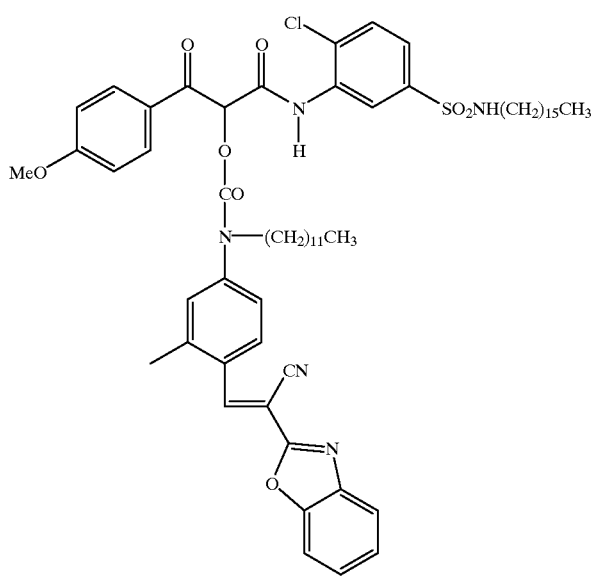
Comp-4
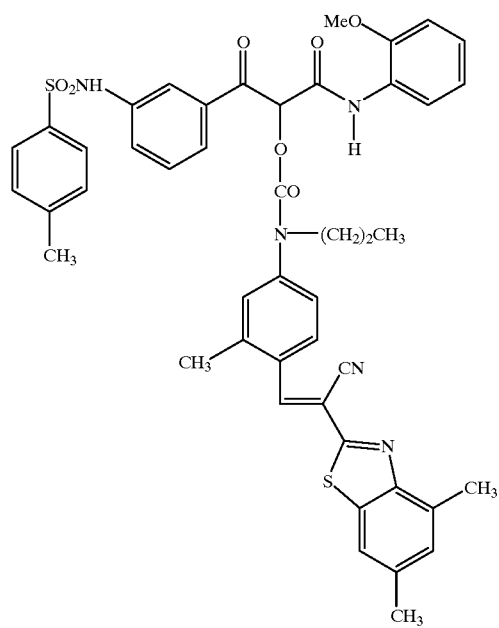

Comp-5
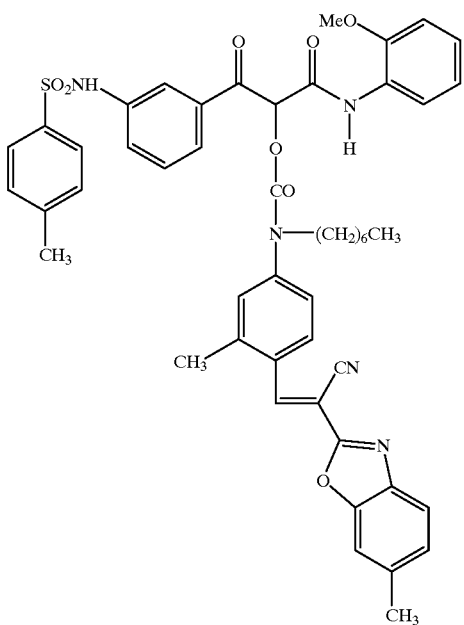
Comp-6
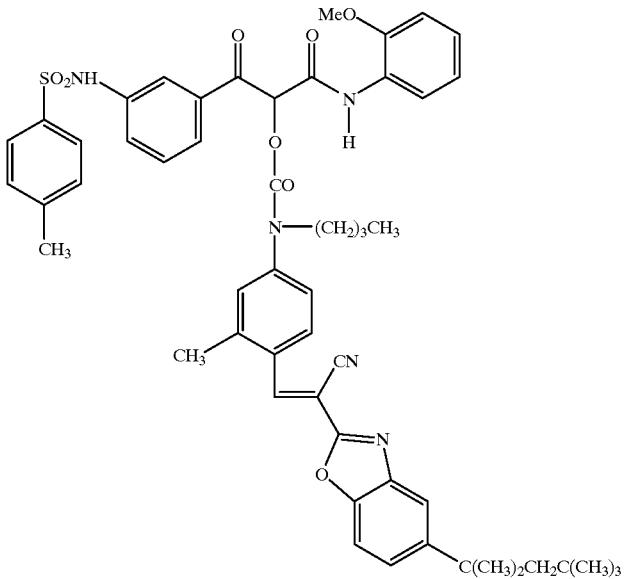
Comp-7
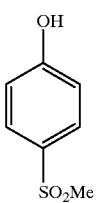

-continued
Comp-8
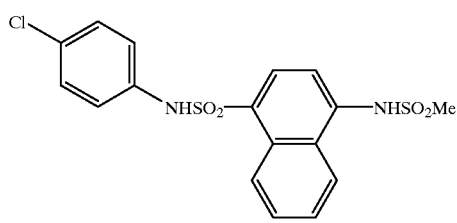
Comp-9
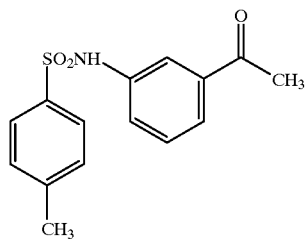
Comp-10
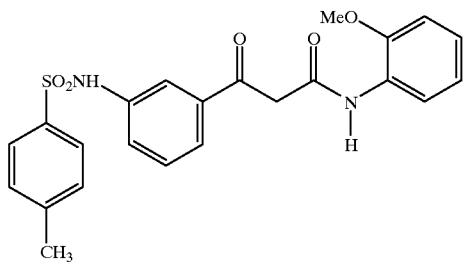
Comp-11
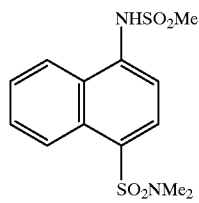
Comp-12
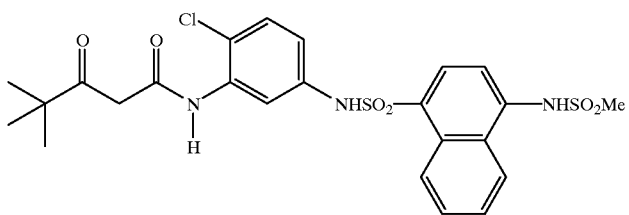

-continued
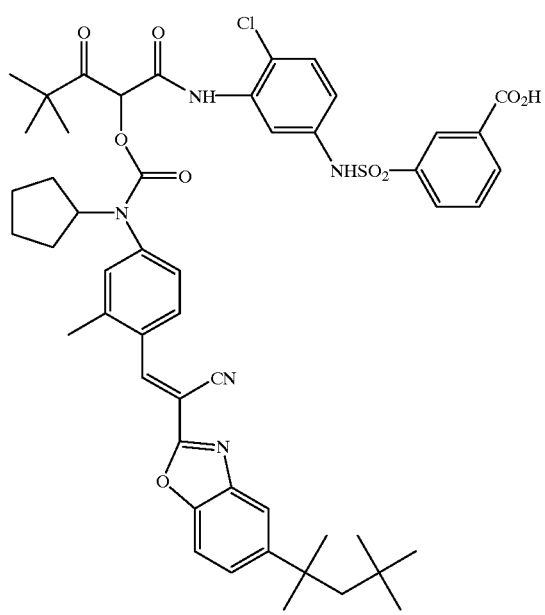
Comp-13
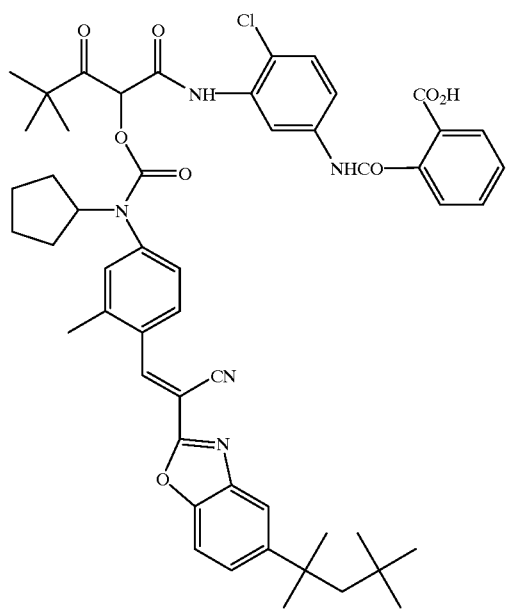
Comp-14

-continued
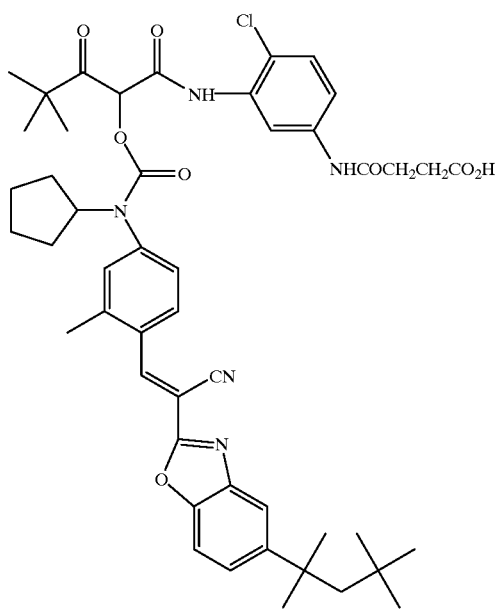
Comp-15
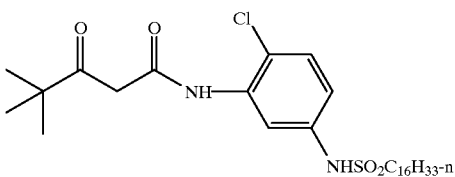
Comp-16
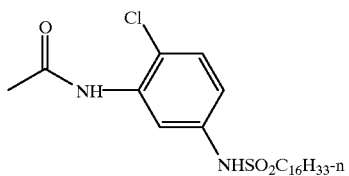
Comp-17
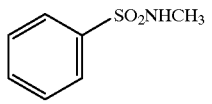
Comp-18
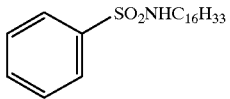
Comp-19
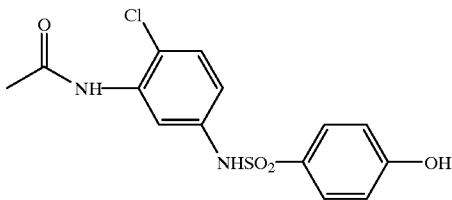
Comp-20

-continued

Comp-21

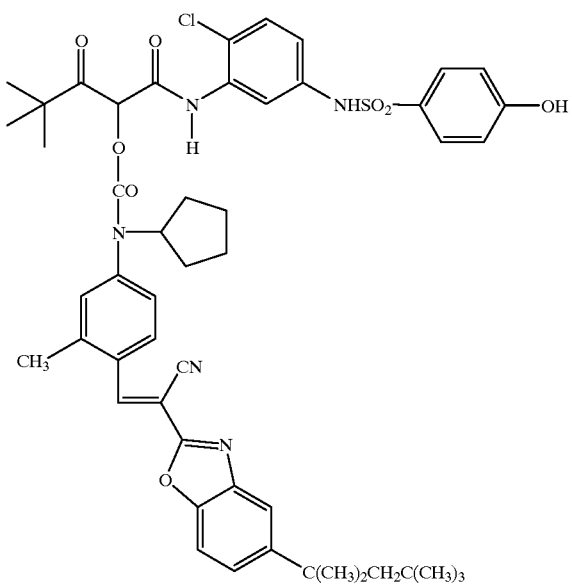

The samples were tested as shown in the footnotes of Table I, and the results of the testing are as shown.

TABLE I

| Sample | Coupler | Reference/ sol group | C log P* | pKa** | % gamma (vs. C-1)*** | Dmax/Dmax (vs. C-1)**** |
|---|---|---|---|---|---|---|
| 1 | Comp-1 | US 4,840,884 Ex. 40/ ArNHSO$_2$ | 9.3 | 9.5 | 38 | 0.62 |
| 2 | Comp-2 | US 5,457,004 Ex. I-5/ SO$_2$NHC$_{16}$H$_{33}$ | 4.1 | 13 | 14 | 0.24 |
| 3 | Comp-3 | US 5,457,004 Ex. I-4/ SO$_2$NHC$_{16}$H$_{33}$ | 8.1 | 13 | 29 | 0.44 |
| 4 | Comp-4 | US 5,457,004 Ex. I-46/ SO$_2$NHAr | 4.6 | 8.8(e) | (e) | (e) |
| 5 | Comp-5 | NHSO$_2$ | 6.1 | 8.8 | 69 | 1.07 |
| 6 | Comp-6 | " | 7.9 | 8.9 | 82 | 1.21 |
| 7 | Comp-21 | ArOH | 8.4 | 8.8 | 98 | 1.18 |
| 8 | Inv-1 | ArOH/NHSO$_2$ | 8.4 | 7.2 | 145 | 1.40 |
| 9 | Inv-3 | ArOH | 8.4 | 8.7 | 166 | 1.59 |
| 10 | Inv-4 | NHSO$_2$ | 6.9 | 6.5 | 150 | 1.52 |
| 11 | Inv-5 | " | 6.9 | 6.7 | 199 | 1.68 |
| 12 | Inv-6 | ArOH/NHSO$_2$ | 8.4 | 7.4 | 168 | 1.59 |
| 13 | Inv-7 | NHSO$_2$ | 6.9 | 7.9 | 183 | 1.56 |
| 14 | Inv-8 | " | 6.9 | 6.1 | 158 | 1.53 |
| 15 | Inv-9 | " | 8.4 | 7.9 | 110 | 1.39 |
| 16 | Inv-10 | " | 8.4 | 6.1 | 204 | 1.84 |

*calculated log partition coefficient for the coupled-off dye using literature values (A. Leo, C. Hansch, and D. Elkins, Chemical Reviews, 71, p525,1971)
**measured in aqueous Triton X-100 solution
***(coupler contrast/C-1 reference coupler contrast) x 100; all examples dispersed in dibutyl phthalate except for example 16 (oleyl alcohol)
****Coupler Dmax/Dmax of reference coupler C-1
(a)Comp-1 and reference coupler C-1 were each coated at 1.3 mmoles/m$^2$ in this sample.
(b)Comp-2 and Comp-3 were each coated at 0.20 mmoles/m$^2$ and reference coupler C-1 was coated at 0.40 mmoles/m$^2$ for these two samples.
(c)Comp-5 and Comp-6 were each coated at 0.2 mmoles/m$^2$ and reference coupler C-1 was coated at 0.4 mmoles/m$^2$ for these two samples.
(d)Inv-1 through Inv-10 were all coated at 0.27 mmoles/m$^2$ and compared to reference coupler C-1 coated at 0.54 mmoles/m$^2$.
(e)pKa is inferred from Comp-5 and Comp-6; gamma and Dmax not meaningful because of excessive wash out of mobile methine dye.

The data of Table I show a clear superiority when using the coupler of the invention possessing the desired solubilizing group. The inventive samples exhibit a gamma value generally exceeding the gamma of the comparison by 50% or more. Similarly, the compounds of the invention provide a maximum density (Dmax) generally 40% or more than the comparisons.

The data for Comp-1, 2, and 3 illustrate the state of the art for HDY couplers that release a second dye via an acyloxy group. The reactivity is very low even though sulfonamide solubilizing groups are present. For example, Comp-2 demonstrates the effect of a diffusible release dye washing out of the coating and lowering contrast and Dmax so much that meaningful comparisons are obtainable only with non-diffusing dyes. In general, dyes that have C log P values less than about 6 exhibit some washout.

Example I-46 in U.S. Pat. No. 5,457,004 (Comp-4) contains a sulfonamide function but the C log P is too low to prevent washout of the second methine dye. Comp-5 and Comp-6 contain the same solubilization with immobile dyes and do provide higher contrast and Dmax consistent with enhanced reactivity but the contrast is still far less than desired. Sulfonamide pKa values of 8.8 and 8.9 were measured for these two couplers.

Couplers of this invention (Inv-1–10) demonstrate greater reactivity increases as the fraction of ionized sulfonamide increases.

Phenolic solubilization can be effective as demonstrated by Inv-1, 3, and 6.

Example 2

The pKa data in Table II for simpler compounds shows that the sulfonamide function may provide a pKa value ranging from 6 to 13. The more acidic values are useful for improving coupler activity. Comp-10 has a pKa at the coupling site of 10.3.

TABLE II

| Compound | pKa (Sol. group)* |
| --- | --- |
| Comp-7 | 7.8** |
| Comp-9 | 8.7 |
| Comp-10 | 8.8 |
| Comp-11 | 6.6 |
| Comp-12 | 6.8 |
| Comp-16 | 9.4 |
| Comp-17 | 9.5 |
| Comp-18 | 11.43*** |
| Comp-19 | 13.0 |
| Comp-20 | 8.1 |

*measured in aqueous Triton X-100
**measured in water (Bordwell and Cooper, J. Amer. Chem. Soc., 1952, 74, 1058)
***measured in water (King, J. f., in The Chemistry of Sulphonic Acids, Esters, and their Derivatives, Patai, S., ed; Interscience Publishers: Essex, 1991, pp 249–259.

Example 3

Sulfonamide vs Carboxylic Acid Solubilization.

Experimental

Samples of each element were imagewise exposed through a graduated density test object and processed at 40° C., employing a color developing solution as described below, then bleached, fixed, and dried to produce yellow dye images.

$K_2SO_3$: 2.0 gm,
$K_2CO_3$: 30.0 gm,
KBr: 1.25 gm,
KI: 0.6 mg,
4-Amino-3-methyl-N-ethyl-N-β'-hydroxyethylaniline sulfate: 3.55 gm,
Water to 1.0 liter, pH 10.0.

The processing steps and corresponding times for both the standard and accelerated processes are given in Table III.

TABLE III

| Processing step | Standard process | Accelerated process |
| --- | --- | --- |
| Developer | 3 min 15 sec | 2 min |
| Bleach | 4 min | 30 sec |
| Wash | 3 min | 15 sec |
| Fix | 4 min | 30 sec |
| Wash | 3 min | 15 sec |

The high boiling solvents used in the experiments are given in the table below.

TABLE IV

| solvent | chemical name |
| --- | --- |
| Sol. 1 | 2-hexyl-1-decanol |
| Sol. 2 | tri-2-ethylhexyl phosphate |
| Sol. 3 | phenethyl benzoate |
| Sol. 4 | 1,4-cyclohexylenedimethylenebis(2-ethylhexanoate) |
| Sol. 5 | di-n-butyl sebacate |
| Sol. 6 | di-n-butylphthalate |

Sulfonamide solubilization produces dyes which are not prone to washout under neutral conditions. By contrast, carboxylic acid solubilization leads to the formation of dyes that are subject to washout under neutral conditions, i.e, in water rinse steps of the photographic process. This leads to higher Dmax values (more retained azomethine dye) for the sulfonamide solubilized materials.

A series of experiments were conducted in order to determine the factors involved in the relatively low Dmax values observed for carboxylic acid solubilized HDY couplers as compared to sulfonamide solubilized HDY couplers. On the basis of these experiments, it was concluded that the carboxylic acid solubilized couplers yielded dyes subject to washout under neutral conditions. Table 1 contains a list of Dmax values (sensitometry) for a series of HDY couplers and the relative amounts of azomethine dye (HPLC). In each case the relative yield of carboxylic acid solubilized dye is lower than that of the sulfonamide solubilized dye. Even the least reactive of the sulfonamide solubilized couplers (Inv-9), which has unreacted coupler in the Dmax region yields more azomethine dye than the best of the carboxylic acid solubilized couplers (Comp-13) which contains no unreacted coupler in the Dmax region.

TABLE V

| Compound[a] | High boiling solvent[b] | Azomethine dye in Dmax (HPLC)[c] | Dmax |
| --- | --- | --- | --- |
| Inv-42 | Sol. 2 | 0.78 | 1.51 |
| Inv-42 | Sol. 3 (50%): Sol. 4 (50%) | 0.76 | 1.44 |
| Inv-42 | Sol. 5 | 0.68 | 1.42 |
| Inv-9 | Sol. 6 | 0.54 | 1.35 |
| Comp-13 | Sol. 6 | 0.51 | 1.35 |
| Comp-14 | Sol. 6 | 0.26 | 1.02 |
| Comp-15 | Sol. 6 | 0.21 | 1.26 |

[a]Standard exposure and processing conditions are given in the Experimental section.
[b]Table IV contains a list of the high boiling solvents.
[c]Relative amounts of azomethine dye based on HPLC analysis.

These data indicate that some of the carboxylic acid solubilized dye is lost during processing. On the basis of the relatively low pKa values of the carboxylic acid groups (e.g., pka(benzoic acid=4.2, i.e., at least two pK units more acidic than sulfonamides), we investigated the possibility that the carboxylic acid solubilized dye was subject to washout at near neutral pH values. As a consequence, the carboxylic acid solubilized dye could possibly be subject to washout during bleach, fix, or rinse steps. In order to test this hypothesis, a series of coated film strips were processed under accelerated conditions (see Table III) to minimize any potential dye loss. The strips were then subject to rinse (water) for 20 min. The sensitometric change in the Dmax value after rinse in addition to the % dye lost during rinse are contained in Table VI.

TABLE VI

Azomethine Dye Washout After Rinse (20 min)

| Compound[a] | High boiling solvent[b] | Blue Dmax change[c] | % Azomethine Dye lost[d] |
|---|---|---|---|
| Inv-9 | Sol. 6 | −0.02 | 0 |
| Inv-26 | Sol. 6 | −0.04 | 3 |
| Inv-42 | Sol. 5 | 0.00 | 1 |
| Inv-42 | Sol. 2 | −0.02 | 0 |
| Inv-42 | Sol. 3 (50%): Sol. 4 (50%) | −0.02 | 3 |
| Inv-44 | Sol. 1 | −0.03 | 4 |
| Comp-13[COOH] | Sol. 6 | −0.11 | 13 |
| Comp-14 | Sol. 6 | −0.13 | 39 |
| Comp-15 | Sol. 6 | −0.21 | 51 |

[a]Processed under accelerated conditions, see Table III
[b]Table IV contains a list of the high boiling solvents.
[c]Given by the difference: Dmax(20 min rinse) - Dmax(no rinse).
[d]Determined by HPLC analysis.

The data in Table VI show that carboxylic acid solubilized dyes are subject to washout under neutral conditions. The losses in Dmax for the carboxylic acid solubilized couplers are more than two times that of the sulfonamide solubilized couplers.

Example 4
Multilayer Example

The Multi-layer film structures utilized for the comparison yellow dye forming coupler YC-1 and for the inventive coupler Inv-42 are shown below as Elements 1 and 2. Because of the excellent performance of the inventive coupler, the element 1 was thinned by reducing the levels of imaging components (couplers and silver halide) to give element 2. Element 2 gave equivalent photographic sensitometric response to Element 1 but with considerable component (cost) savings. Component laydowns are provided in units of gr/m$^2$. (Bis-vinylsulfonyl)methane hardener at 2% of total gelatin weight was added as a dual melt to layer 1. Antifoggants (including 4-hydroxy-6-methyl-1,3,3a,7-tetraazaindene), surfactants, coating aids, coupler solvents, emulsion addenda, sequestrants, lubricants, matte and tinting dyes were added to the appropriate layers as is common in the art. Samples of each element were given a stepped exposure and processed in the KODAK FLEXICOLOR (C-41) process as described in *British Journal of Photography Annual*, 1988, pp. 196–198.

Element 1:

Layer 1 (Overcoat/UV Filter Layer): silver bromide Lippmann emulsion at 0.215, UV-1 and UV-2 both at 0.108 and gelatin at 1.237.

Layer 2 (Fast Yellow Layer): a blend of two blue sensitized (with BSD-1) silver iodobromide emulsions (i) 1.4 μm, 14 mole % I, 3d, saturated iodide core coated at 0.902, (ii) 3.3×0.13 μm, 1.5 mole %, tabular, coated at 0.412, yellow dye forming coupler YC-1 at 0.424, IR-1 at 0.027, B-1 at 0.011 and gelatin at 1.70.

Layer 3 (Slow Yellow Layer): a blend of three blue sensitized (all with BSD-1) tabular silver iodobromide emulsions (i) 0.96×0.26 μm, 6 mole % I at 0.233, (ii) 1.0×0.13 μm, 1.5 mole % I at 0.081, (iii)) 0.54×0.08 μm, 1.3 mole % I at 0.394, yellow dye forming coupler YC-1 at 0.733, IR-1 at 0.027, B-1 at 0.003 and gelatin at 1.61.

Layer 4 (Yellow filter layer): YFD-1 at 0.108, OxDS-1 at 0.075 and gelatin at 0.807.

Layer 5 (Fast Magenta Layer): a green sensitized (with a mixture of GSD-1 and GSD-2) silver iodobromide tabular emulsion (3.95–0.14 μm, 3.7 mole % iodide) at 1.29, magenta dye forming coupler MC-1 at 0.084, IR-7 at 0.003 and gelatin at 1.58.

Layer 6 (Mid Magenta Layer): a green sensitized (with a mixture of GSD-1 and GSD-2) silver iodobromide tabular emulsion: (i) 2.85×0.12 μm, 3.7 mole % iodide at 0.969, magenta dye forming coupler MC-1 at 0.082, Masking Coupler MM-1 at 0.086, IR-7 at 0.011 and gelatin at 1.56.

Layer 7 (Slow magenta layer): a blend of two green sensitized (both with a mixture of GSD-1 and GSD-2) silver iodobromide tabular emulsions: (i) 0.88×0.12 μm, 2.6 mole % iodide at 0.537 and (ii) 1.20×0.12 μm, 1.8 mole % iodide at 0.342, magenta dye forming coupler MC-1 at 0.285, Masking Coupler MM-1 at 0.075 and gelatin at 1.18.

Layer 8 (Interlayer): OxDS-1 at 0.075 and gelatin at 0538.

Layer 9 (Fast Cyan layer): a red-sensitized sensitized (with a mixture of RSD-1 and RSD-2) iodobromide tabular emulsion (4.0×0.13μm, 4.0 mole % I) at 1.291, cyan dye-forming coupler CC-2 at 0.205, IR-4 at 0.025, IR-3 at 0.022, OxDS-1 at 0.014 and gelatin at 1.45.

Layer 10 (Mid Cyan Layer): a red-sensitized (all with a mixture of RSD-1 and RSD-2) iodobromide tabular emulsion (2.2×0.12 μm, 3.0 mole % I) at 1.17, cyan dye-forming coupler CC-2 at 0.181, IR-4 at 0.011, masking coupler CM-1 at 0.032, OxDS-1 at 0.011 and gelatin at 1.61.

Layer 11 (Slow cyan layer): a blend of two red sensitized (all with a mixture of RSD-1 and RSD-2) silver iodobromide emulsions: (i) a larger sized iodobromide tabular grain emulsion (1.2×0.12μm, 4.1 mole % I) at 0.265, (ii) a smaller iodobromide tabular emulsion (0.74×0.12 μm), 4.1 mole % I) at 0.312, cyan dye-forming coupler CC-1 at 0.227, CC-2 at 0.363, masking coupler CM-1 at 0.032, bleach accelerator releasing coupler B-1 at 0.080 and gelatin at 1.67.

Layer 12 (Interlayer): OxDS-1 at 0.075 and gelatin at 1.35.

Layer 14 (Antihalation layer): Black Colloidal Silver at 0.344, and gelatin at 2.44.

Element 2:

This was identical to Element 1 with the following exceptions:

Layer 2 (Fast Yellow Layer): Silver iodobromide emulsions (i) 1.4 μm, 14 mole % I, 3d, saturated iodide core coated at 0.437, (ii) 3.3×0.13 μm, 1.5 mole %, tabular, coated at 0.198, coupler YC-1 replaced by Inv-42 at 0.146, B-1 omitted, and gelatin at 1.18.

Layer 3 (Slow Yellow Layer): Silver iodobromide emulsions (i) 0.96×0.26 μm, 6 mole % I at 0.108, (ii) 1.0×0.13 μm, 1.5 mole % I at 0.043, (iii) ) 0.54×0.08 μm, 1.3 mole % I at 0.186, yellow dye forming coupler YC-1 replaced by Inv-42 at 0.406, IR-1 at 0.034, B-1 at 0.003 and gelatin at 1.18.

Layer 5 (Fast Magenta Layer): Silver iodobromide tabular emulsion (3.95×0.14 μm, 3.7 mole % iodide) at 1.10, magenta dye forming coupler MC-1 at 0.071, and gelatin at 1.51.

Layer 6 (Mid Magenta Layer): Silver iodobromide tabular emulsion: (i) 2.85×0.12 μm, 3.7 mole % iodide at 0.823, magenta dye forming coupler MC-1 at 0.058, and gelatin at 1.45.

Layer 7 (Slow magenta layer): Silver iodobromide tabular emulsions: (i) 0.88×0.12 μm, 2.6 mole % iodide at 0.414 and (ii) 1.20×0.12 μm, 1.8 mole % iodide at 0.295, magenta dye forming coupler MC-1 at 0.271, and gelatin at 1.08.

Layer 9 (Past Cyan layer): Iodobromide tabular emulsion (4.0×0.13 μm, 4.0 mole % I) at 0.907, cyan dye-forming coupler CC-2 at 0.172, and gelatin at 1.31.

Layer 10 (Mid Cyan Layer): Iodobromide tabular emulsion (2.2×0.12 μm, 3.0 mole % I) at 0.882, cyan dye-forming coupler CC-2 at 0.172, and gelatin at 1.40.

Layer 11 (Slow cyan layer): Silver iodobromide emulsions: (i) a larger sized iodobromide tabular grain emulsion (1.2×0.12 μm, 4.1 mole % I) at 0.194, (ii) a smaller iodobromide tabular emulsion (0.74×0.12 μm), 4.1 mole % I) at 0.263, cyan dye-forming coupler CC-1 at 0.187, CC-2 at 0.281.

Chemical Structures

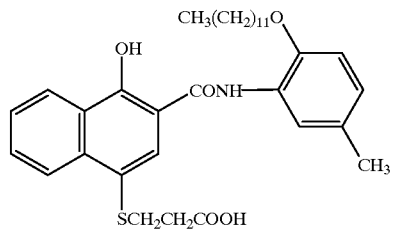

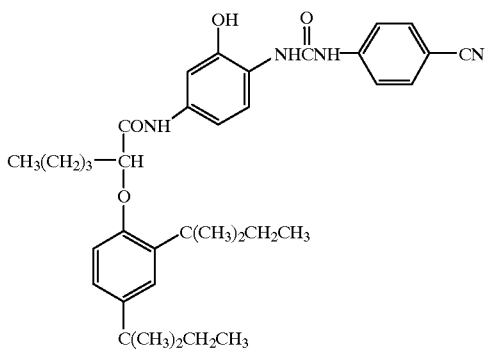

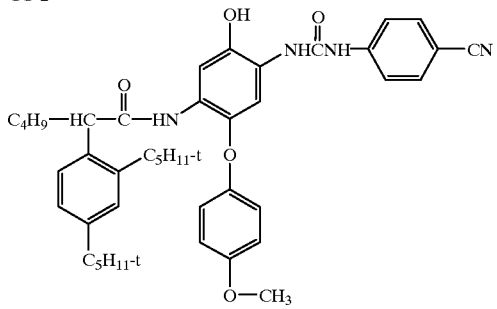

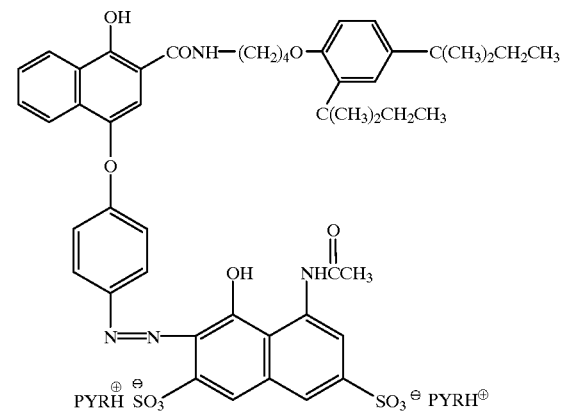

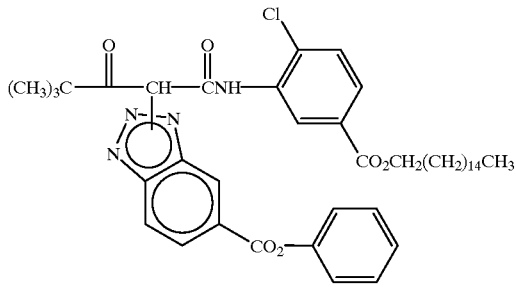

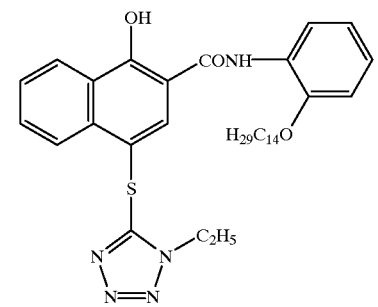

IR-4
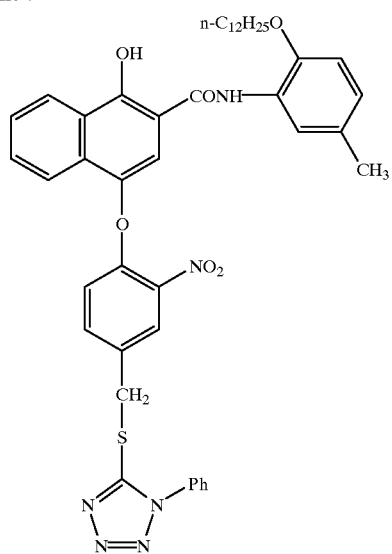
IR-7
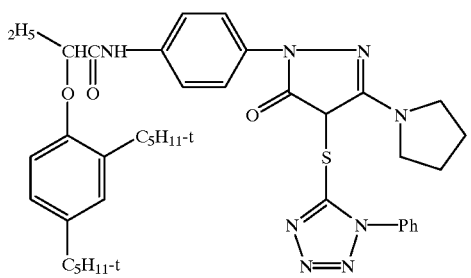
MC-1
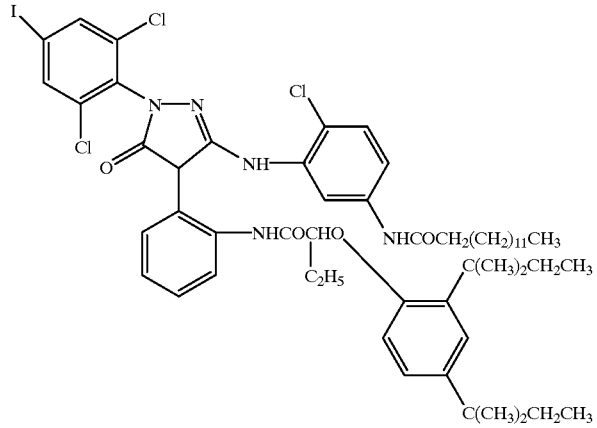
MM-1
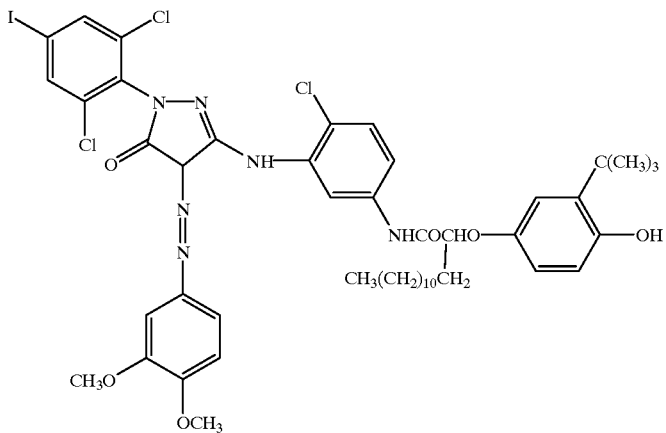
OxDs-1
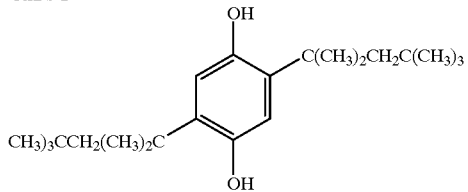
UV-1
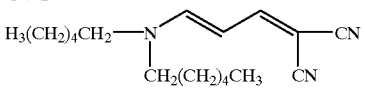

-continued
UV-2
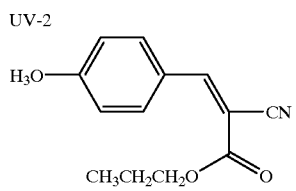
YC-1
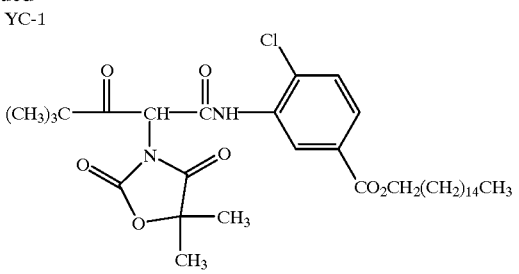
YFD-1
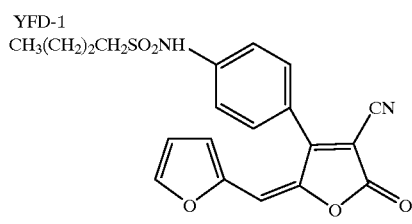
BSD-1
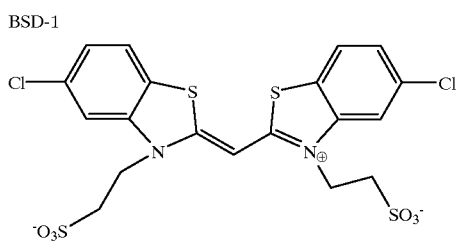
GSD-1
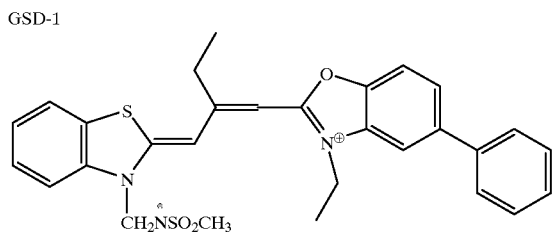
GSD-2
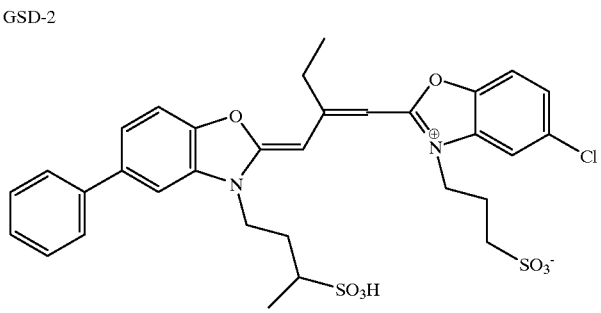
RSD-1
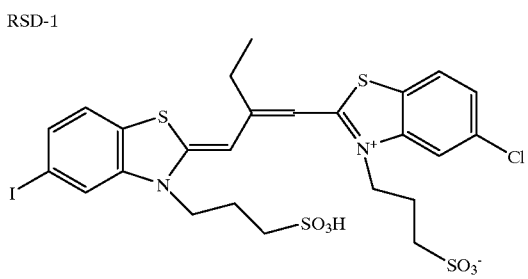
RSD-2
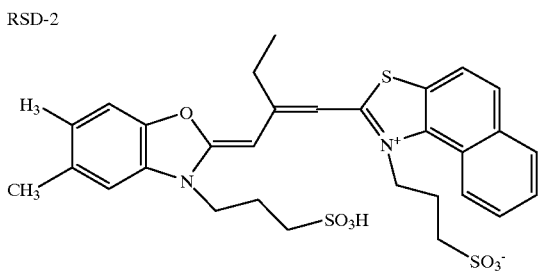
The sensitometric responses were measured for Element 2 (containing the inventive yellow dye form-ing coupler) relative to Element 1 (containing the conventional yellow dye formning coupler). Elements were given a neutral exposure. Change in speed was measured at 0.15 density above Dmin:

TABLE VII

| Layer | Delta speed | Delta Gamma |
|---|---|---|
| Red Light Sensitive Layers | +0.01 Log E | +6% |
| Green Light Sensitive Layers | +0.03 Log E | −3% |
| Blue Light Sensitive Layers | no change | −4% |

It can be seen from this data that the responses of the two elements are very similar, in spite of the fact that Element 2 contains less than 80% of the silver halide and much lower levels of gelatin and of imaging couplers than are present in Element 1. This is made possible by the performance of the inventive coupler. Other improvements in image structure (improved acutance) and in the response of the element to photographic processing (for example, greater developability, easier fixing, less sensitizing dye retention) are also possible by the use of the inventive couplers.

The entire contents of the patents and other publications referred to in this specification are incorporated herein by reference.

What is claimed is:

1. A photographic element containing a light sensitive silver halide emulsion layer having associated therewith a coupler represented by Formula I:

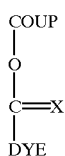

I wherein

COUP is a coupler parent group capable of reacting with an oxidized developer to form a first dye and is bonded at a coupling position to the group

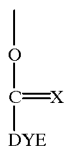

wherein X is O or $NSO_2R$; R is an alkyl or aryl group; and DYE is a releasable second dye that is after release the same color as the first dye and is linked to OC=X by a moiety of the DYE having Formula (IA):

IA wherein $R^2$ is a substituent;
provided there is contained in the coupler of Formula I at least one group of Formula IB:

IB wherein L is a divalent linking group and m is 0 or 1; and Sol is a group containing an acidic hydrogen selected from the group consisting of —ArOH, —$NHSO_2R^1$ and —$SO_2NHR^1$, in which Ar is an aromatic group and each $R^1$ is a substituent;
provided further that the pKa of an acidic hydrogen of Sol is less than 8.8.

2. The element of claim 1 wherein the pKa of the acidic hydrogen of Sol is not less than 5.0.

3. The element of claim 2 wherein the pKa of the acidic hydrogen of Sol is from 5.5 to 8.5.

4. The element of claim 3 wherein the pKa of the acidic hydrogen of Sol is from 6.0 to 8.0.

5. The element of claim 1 wherein Sol is an $NHSO_2R^1$ group in which $R^1$ is an alkyl or aryl group.

6. The element of claim 1 wherein Sol is an $SO_2NHR^1$ group.

7. The element of claim 1 wherein Sol is an ArOH group in which Ar is an aromatic group.

8. The element of claim 1 in which Sol is bonded to the COUP portion of the coupler.

9. The element of claim 1 in which Sol is bonded to the DYE portion of the coupler.

10. The element of claim 1 in which the coupler contains at least two Sol groups, for at least one of which the pKa of the acidic hydrogen of Sol is less than 8.8.

11. The element of claim 1 in which X is O.

12. The element of claim 1 in which DYE is a methine dye.

13. The element of claim 12 in which DYE comprises an electrically neutral dye chromophore.

14. The element of claim 13 in which the DYE contains a benzoxazole group.

15. The element of claim 5 in which there are at least two $NHSO_2R^1$ groups in which each $R^1$ is an independently selected alkyl or aryl group.

16. The element of claim 1 wherein $R^2$ is an alkyl group.

17. The element of claim 16 wherein $R^2$ is selected from the group consisting of methyl, ethyl, isopropyl, butyl, sec-butyl, t-butyl, and cyclopentyl groups.

18. The element of claim 1 wherein COUP is an acylacetanilide.

19. The element of claim 18 wherein COUP is a pivaloylacetanilide.

20. A photographic element containing a light sensitive silver halide emulsion layer having associated therewith a coupler represented by Formula I:

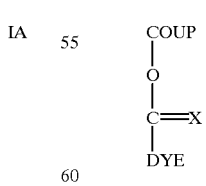

I wherein

COUP is a coupler parent group capable of reacting with an oxidized developer to form a first dye and is bonded at a coupling position to the group

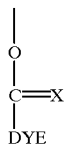

wherein X is O or NSO$_2$R; R is an alkyl or aryl group; and DYE is a releasable non-diffusible second dye that is after release the same color as the first dye and is linked to OC=X by a moiety of the DYE having Formula (IA):

IA wherein R$^2$ is a substituent;
provided there is contained in the coupler of Formula I at least one group of Formula IB:

—L$_m$—Sol   IB wherein L is a divalent linking group and m is 0 or 1; and Sol is a group containing an acidic hydrogen selected from the group consisting of —ArOH, —NHSO$_2$R$^1$ and —SO$_2$NHR$^1$, in which Ar is an aromatic group and each R$^1$ is a substituent;
provided further that the pKa of an acidic hydrogen of Sol is less than 8.8.

21. A photographic element containing a light sensitive silver halide emulsion layer having associated therewith a coupler represented by Formula I:

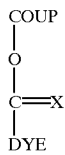

I wherein

COUP is a coupler parent group capable of reacting with an oxidized developer to form a first dye and is bonded at a coupling position to the group

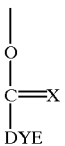

wherein X is O or NSO$_2$R; R is an alkyl or aryl group; and DYE is a releasable second dye having a CLogP of at least 6 that is after release the same color as the first dye and is linked to OC=X by a moiety of the DYE having Formula (IA):

IA wherein R$^2$ is a substituent;
provided there is contained in the coupler of Formula I at least one group of Formula IB:

—L$_m$—Sol   IB wherein L is a divalent linking group and m is 0 or 1; and Sol is a group containing an acidic hydrogen selected from the group consisting of —ArOH, —NHSO$_2$R$^1$ and —SO$_2$NHR$^1$, in which Ar is an aromatic group and each R$^1$ is a substituent;
provided further that the pKa of an acidic hydrogen of Sol is less than 8.8.

22. A photographic element as in claim 21 in which the DYE contains a benzoxazole group.

23. The element of claim 22 wherein the pKa of the acidic hydrogen of Sol is not less than 5.0.

24. The element of claim 22 wherein Sol is an NHSO$_2$R$^1$ group in which R$^1$ is an alkyl or aryl group.

25. The element of claim 22 in which Sol is bonded to the COUP portion of the coupler.

26. The element of claim 22 in which the coupler contains at least two Sol groups, for at least one of which the pKa of the acidic hydrogen of Sol is less than 8.8.

27. The element of claim 22 in which X is O.

28. The element of claim 22 wherein R$^2$ is an alkyl group.

29. The element of claim 1 wherein COUP is an acylacetanilide.

30. The element of claim 18 wherein COUP is a pivaloylacetanilide.

* * * * *